(12) United States Patent
Sauer

(10) Patent No.: US 11,857,174 B2
(45) Date of Patent: Jan. 2, 2024

(54) TISSUE MANIPULATION DEVICE

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 17/945,819

(22) Filed: Sep. 15, 2022

(65) Prior Publication Data

US 2023/0091148 A1 Mar. 23, 2023

Related U.S. Application Data

(60) Provisional application No. 63/335,937, filed on Apr. 28, 2022, provisional application No. 63/245,310, filed on Sep. 17, 2021.

(51) Int. Cl.
*A61B 17/02* (2006.01)
*A61M 25/01* (2006.01)
*A61B 17/00* (2006.01)

(52) U.S. Cl.
CPC ...... *A61B 17/0218* (2013.01); *A61B 2017/00274* (2013.01); *A61B 2017/00323* (2013.01); *A61M 25/0136* (2013.01)

(58) Field of Classification Search
CPC .................................................. A61B 17/0218
USPC ................................................ 600/201–245
See application file for complete search history.

(56) References Cited

U.S. PATENT DOCUMENTS

2003/0176883 A1   9/2003  Sauer et al.
2007/0239162 A1*  10/2007 Bhatnagar .......... A61B 17/8858
                                                    606/86 A

* cited by examiner

*Primary Examiner* — Eduardo C Robert
*Assistant Examiner* — Tara Rose E Carter
(74) *Attorney, Agent, or Firm* — Michael E. Coyne

(57) ABSTRACT

A tissue manipulation device including a securing member pivotably coupled to a handle portion and is pivotably displaceable between an engaged position and a disengaged position. A distal end of a wire is coupled to an end effector of the tissue manipulation device, and the proximal end of the wire is removably coupled to an engagement portion of the securing member when the securing member is in the engaged position and is disengaged from the engagement portion of the securing member when the securing member is in the disengaged position. When the securing member is in the engaged position, the wire couples the securing member and the end effector such that when the securing member is displaced from a first securing member position to a second securing member position, the end effector is displaced from a undeployed position to a deployed position.

19 Claims, 28 Drawing Sheets

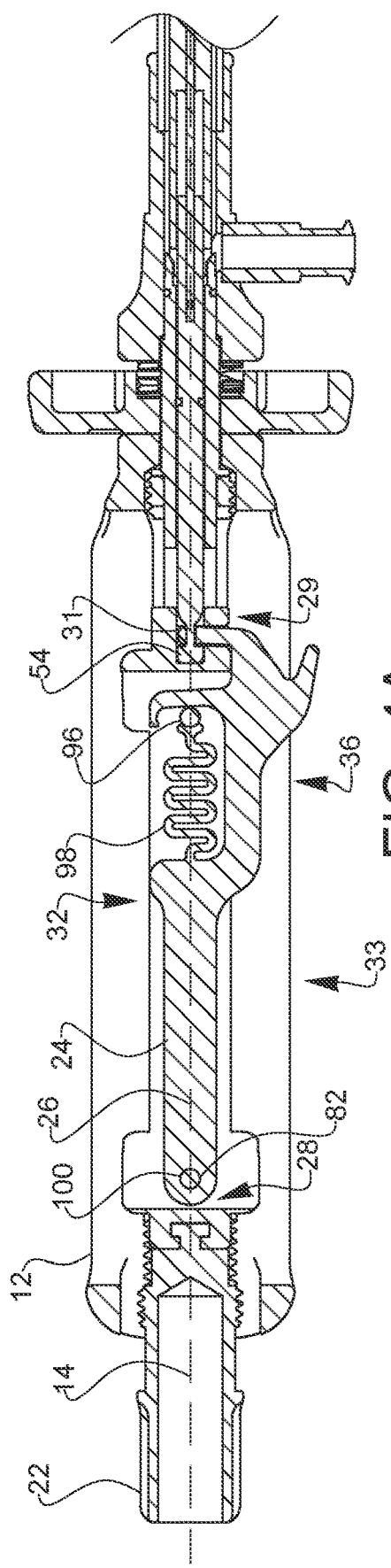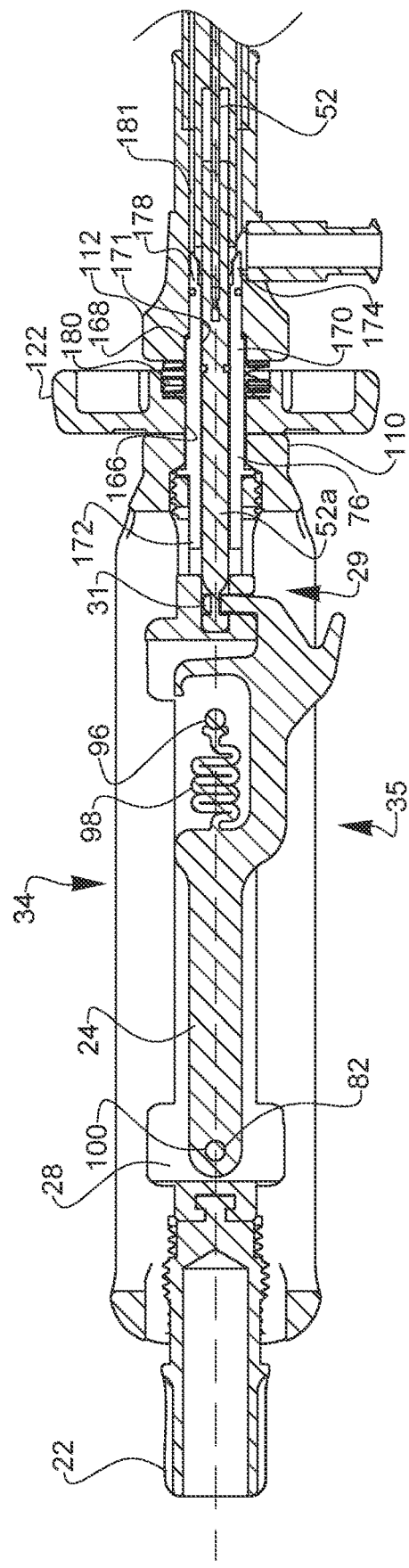

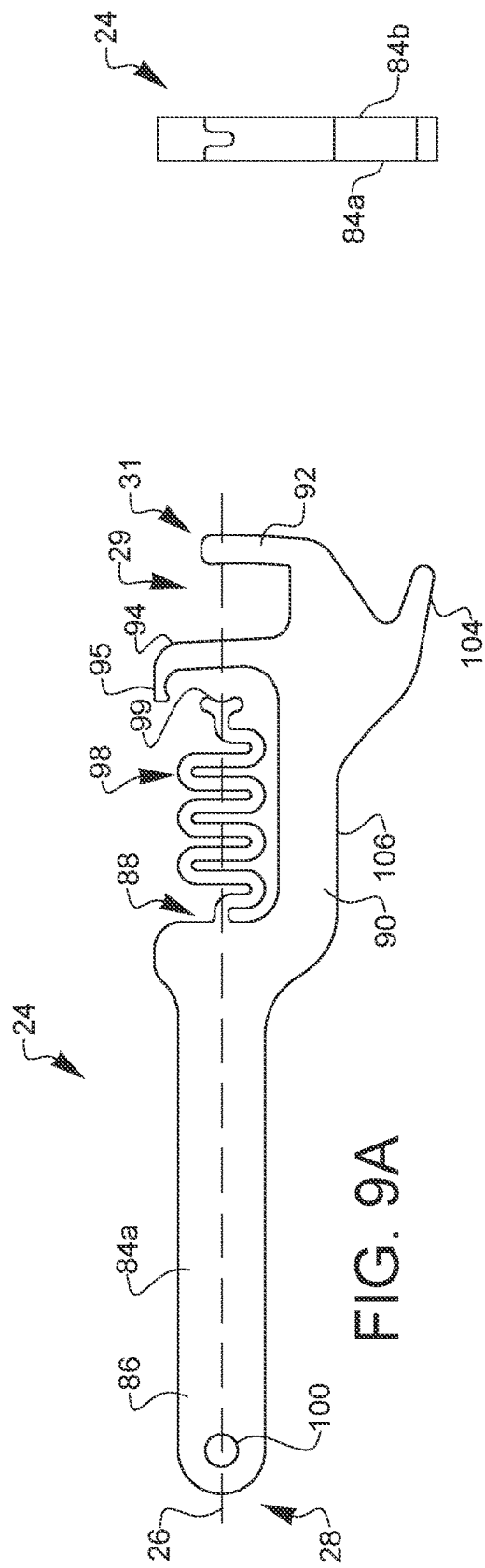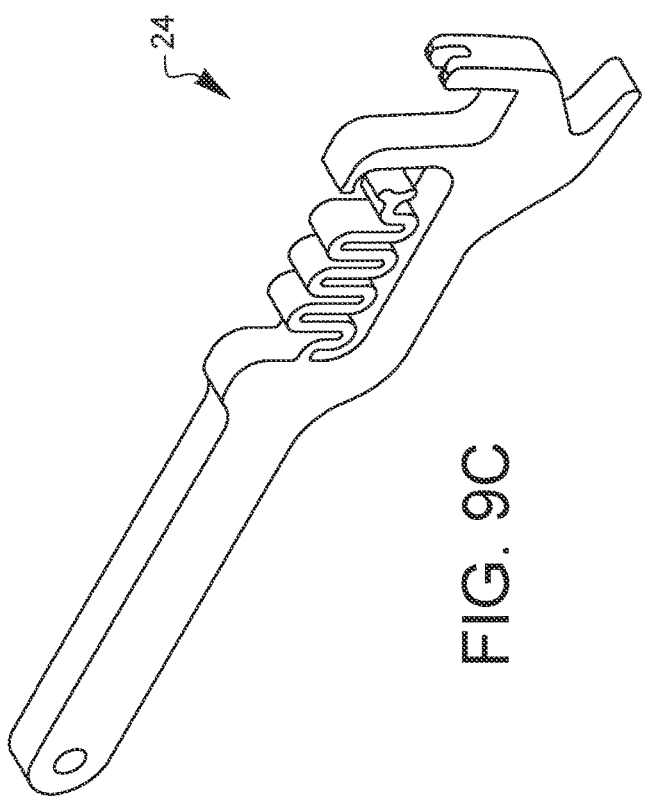

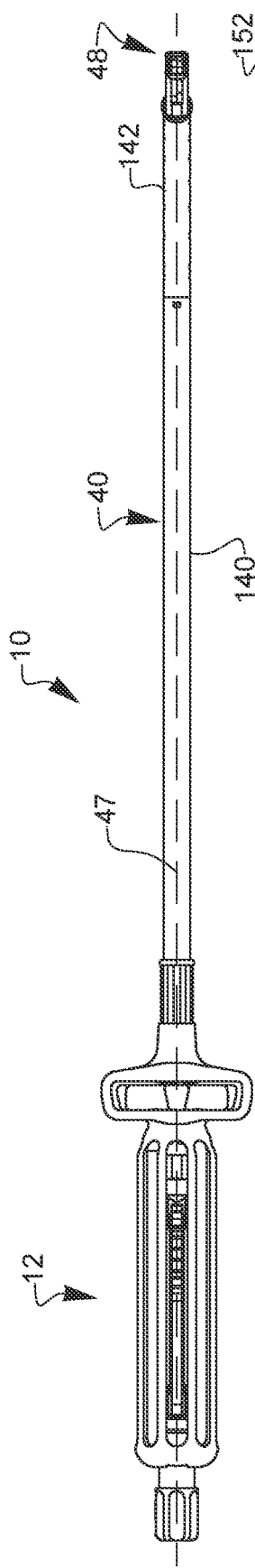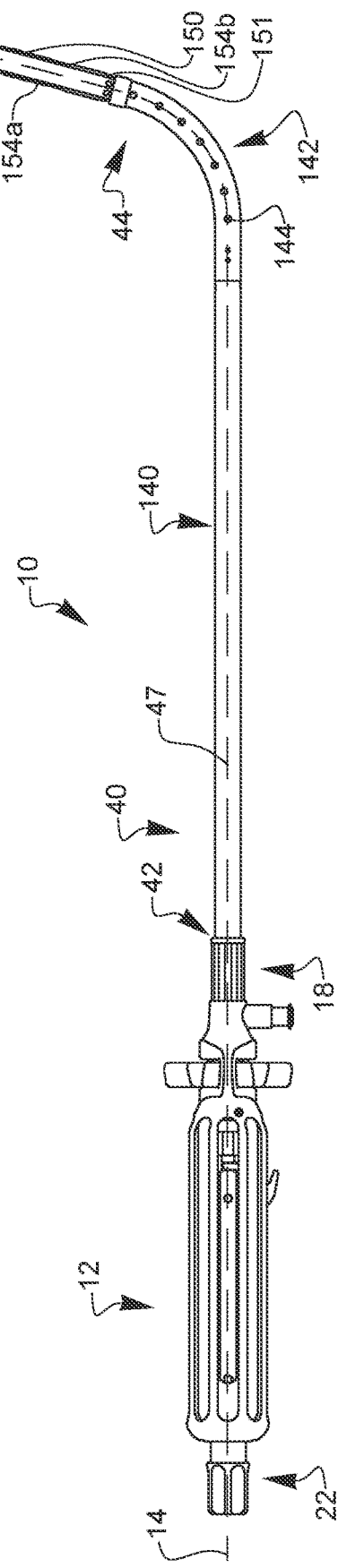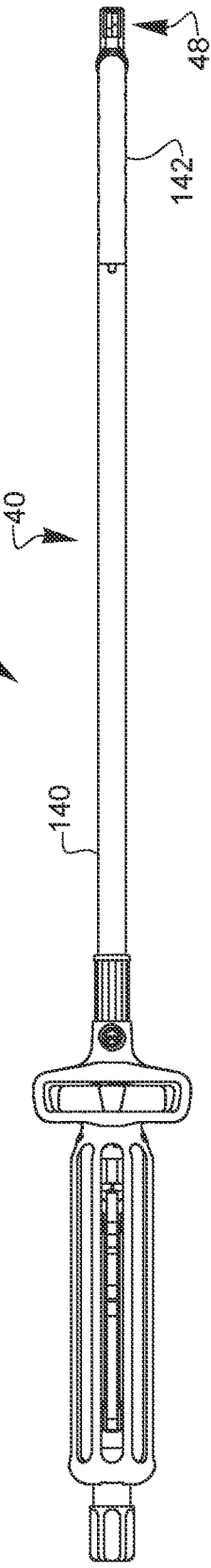
FIG. 10A
FIG. 10B
FIG. 10C

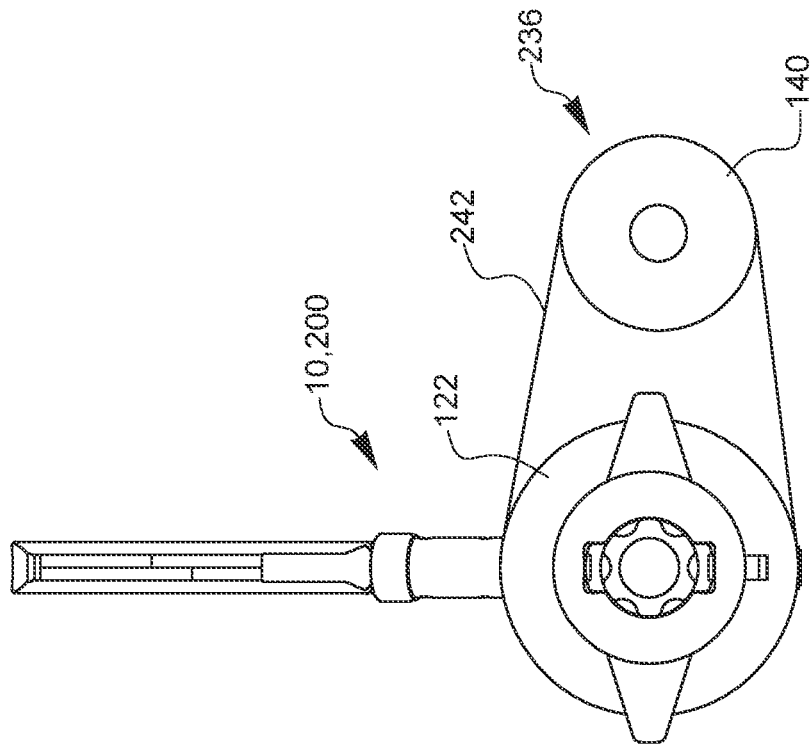
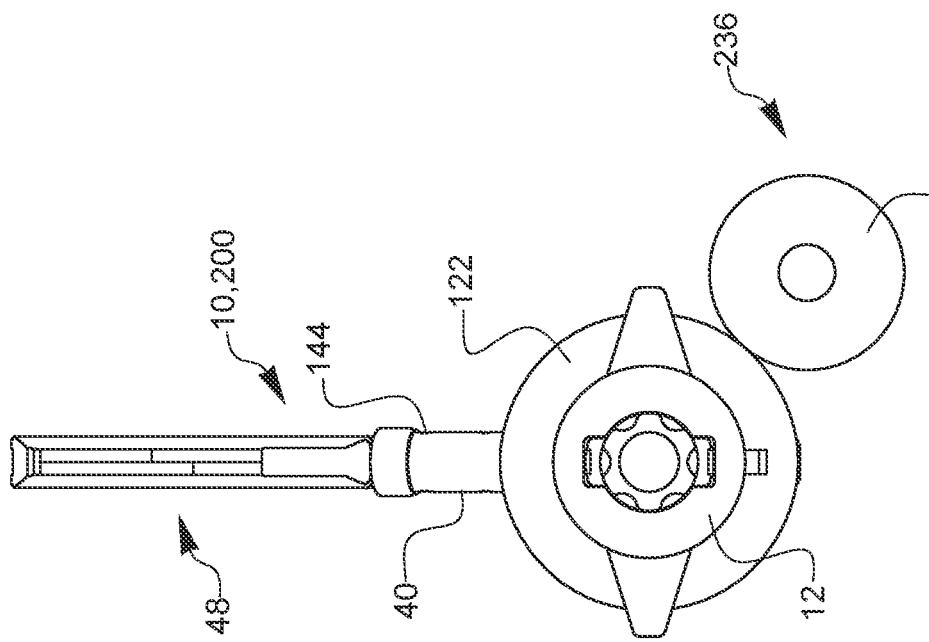

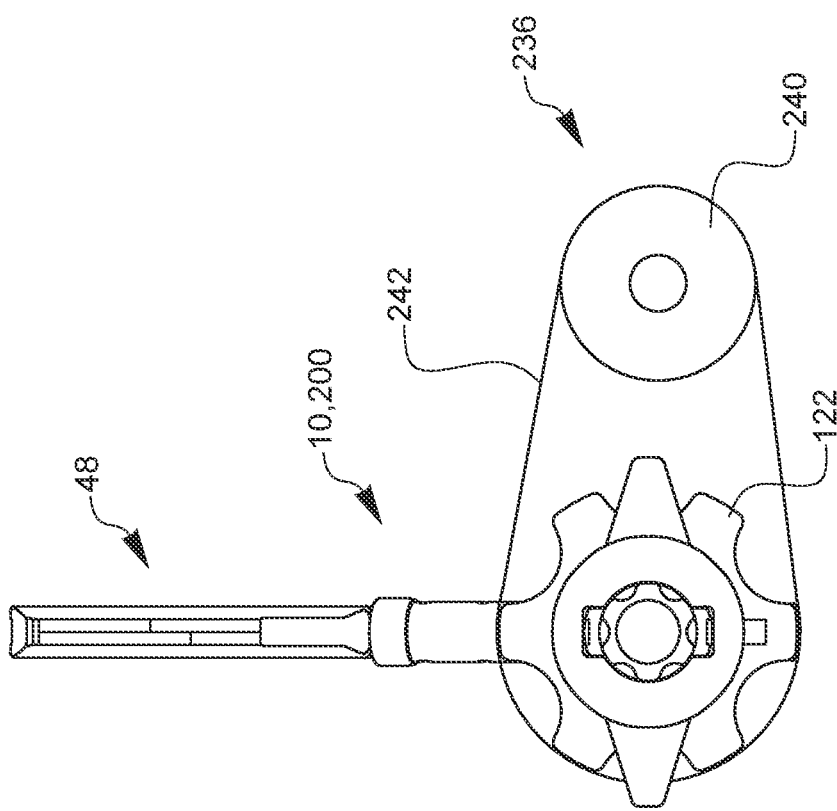

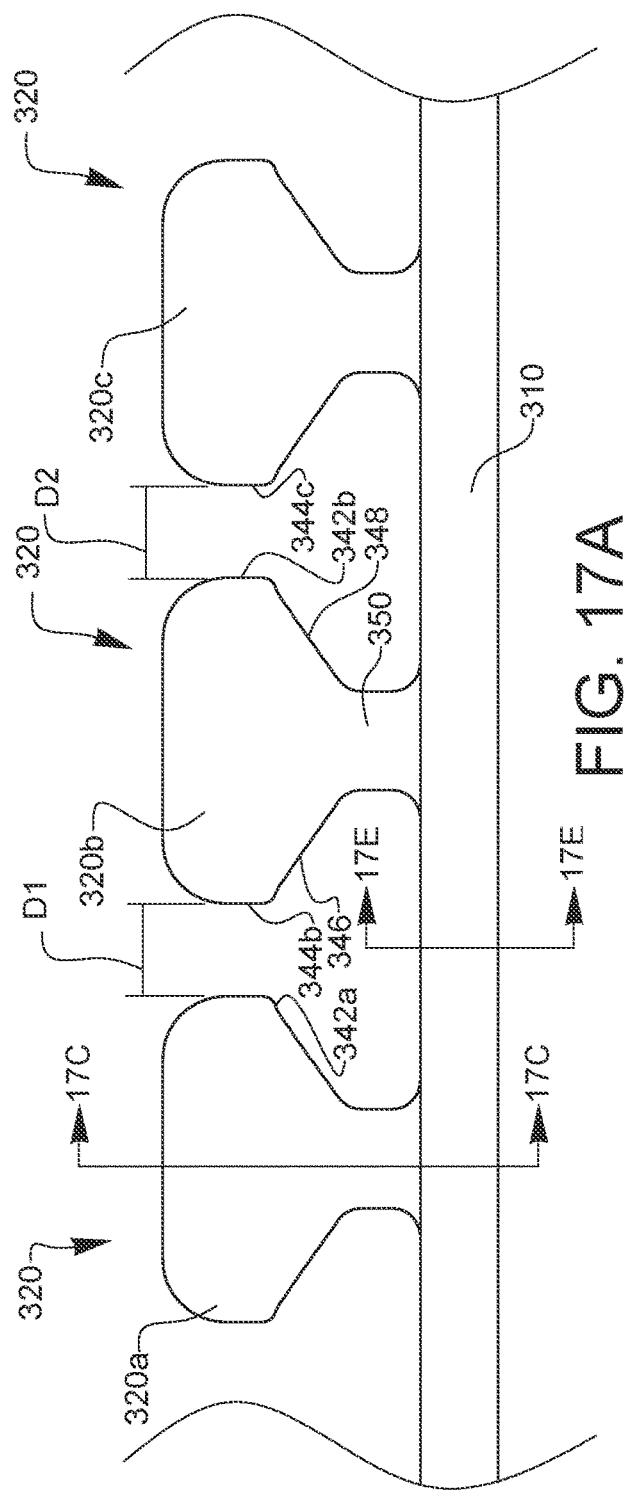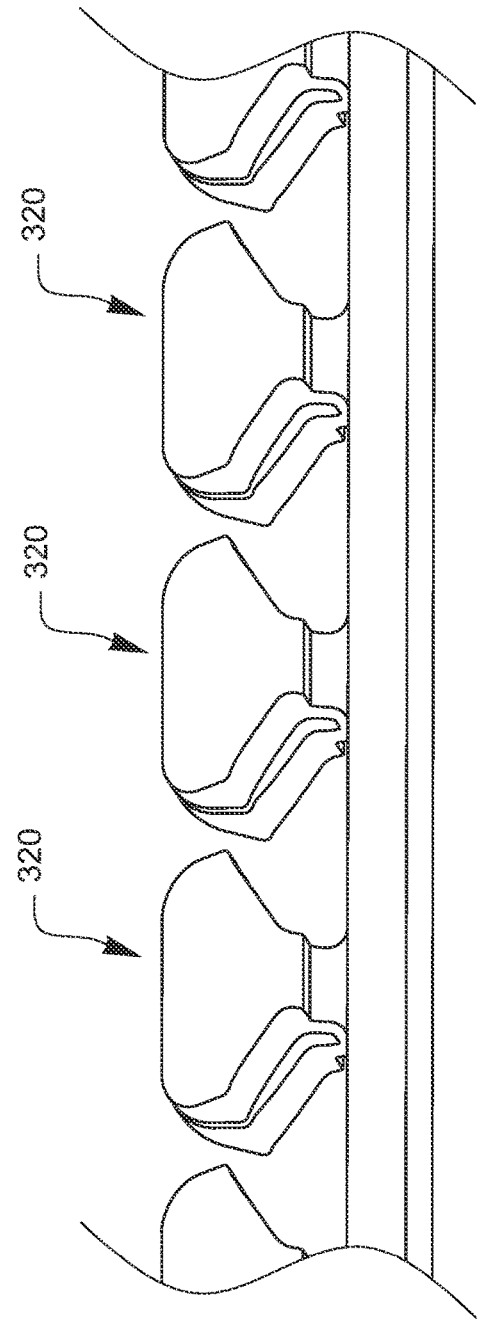
FIG. 17A
FIG. 17B

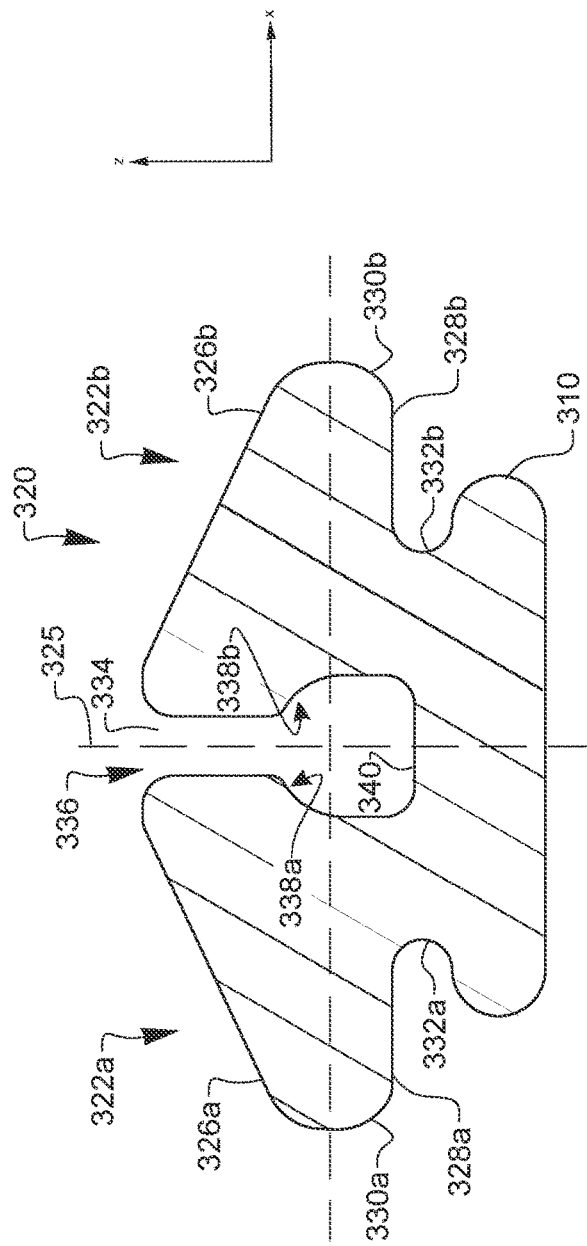
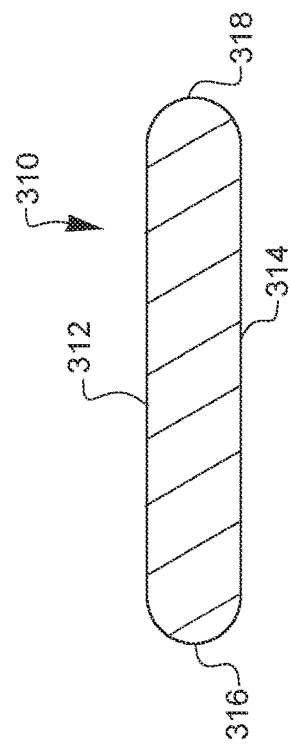
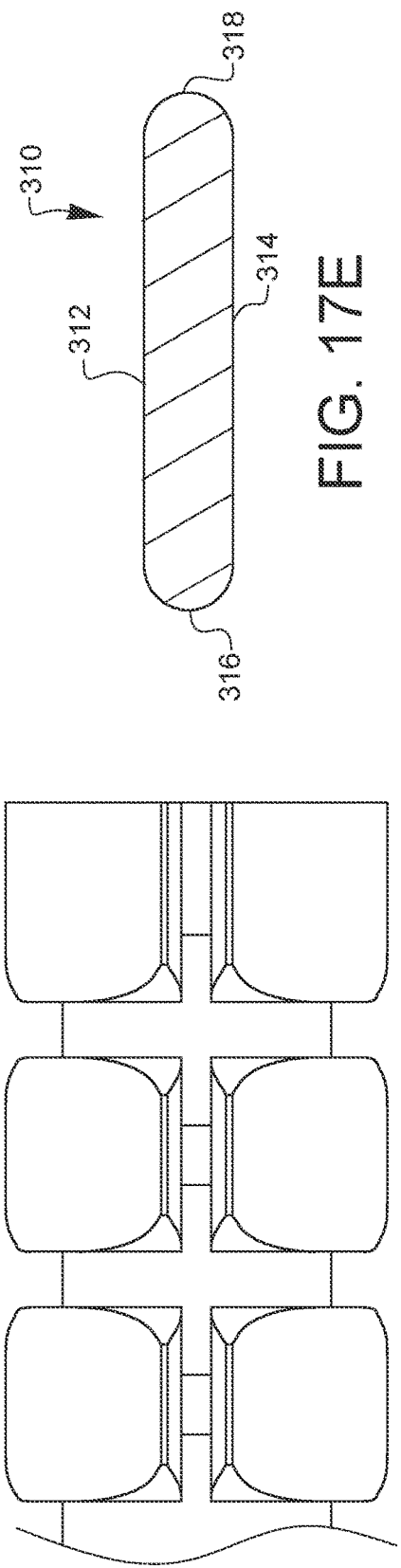

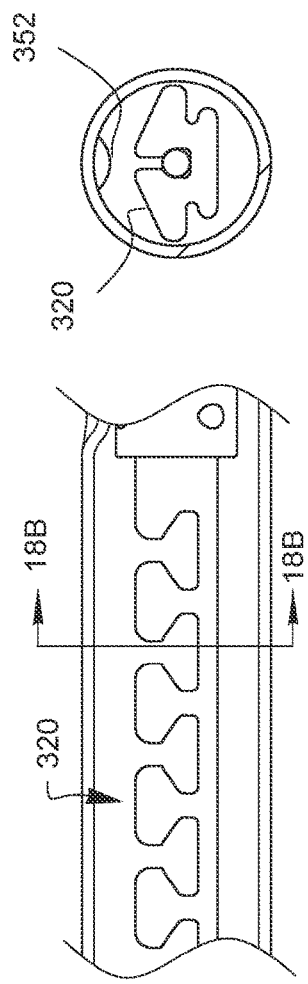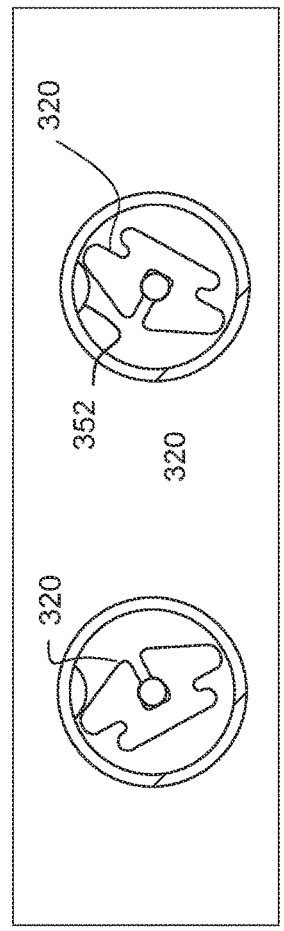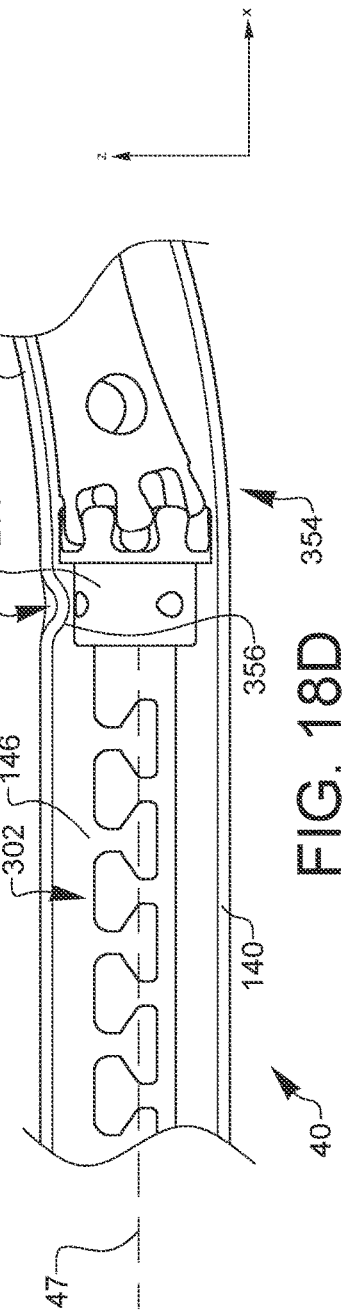

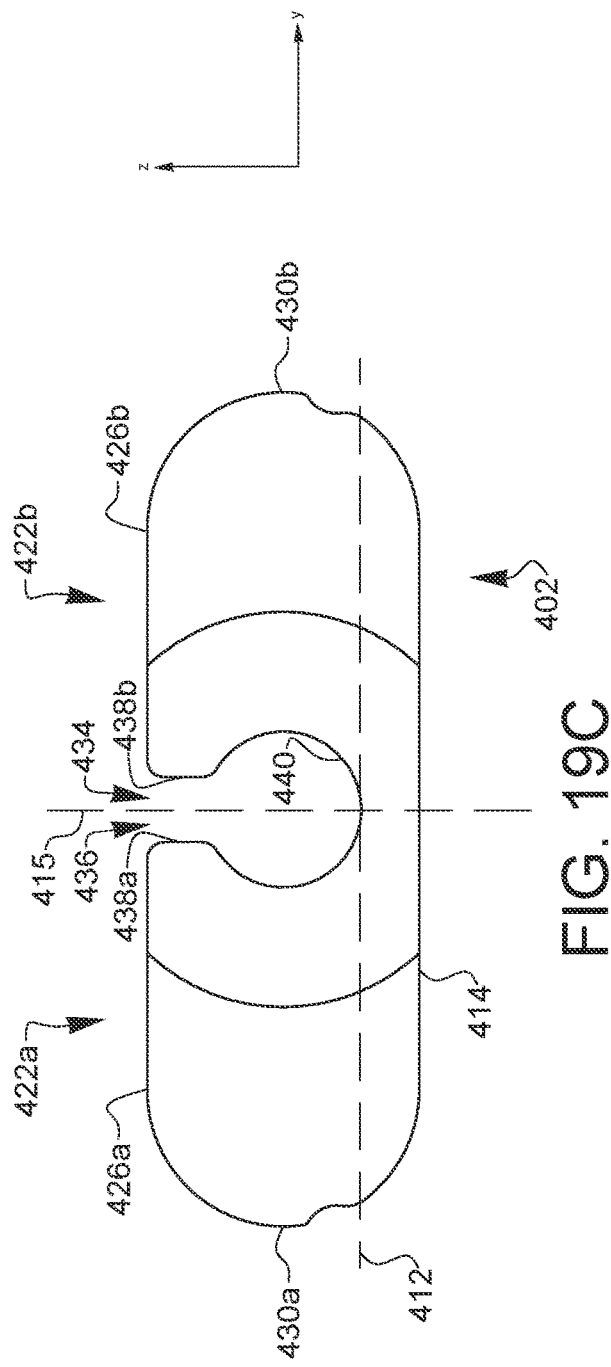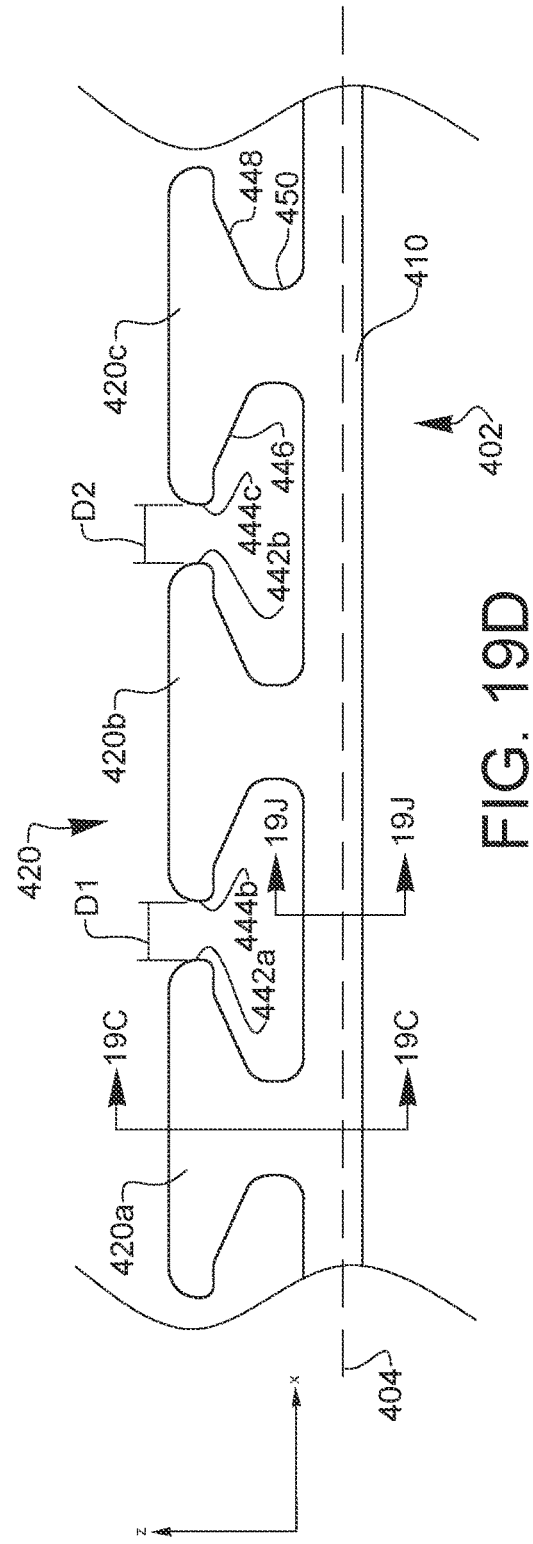

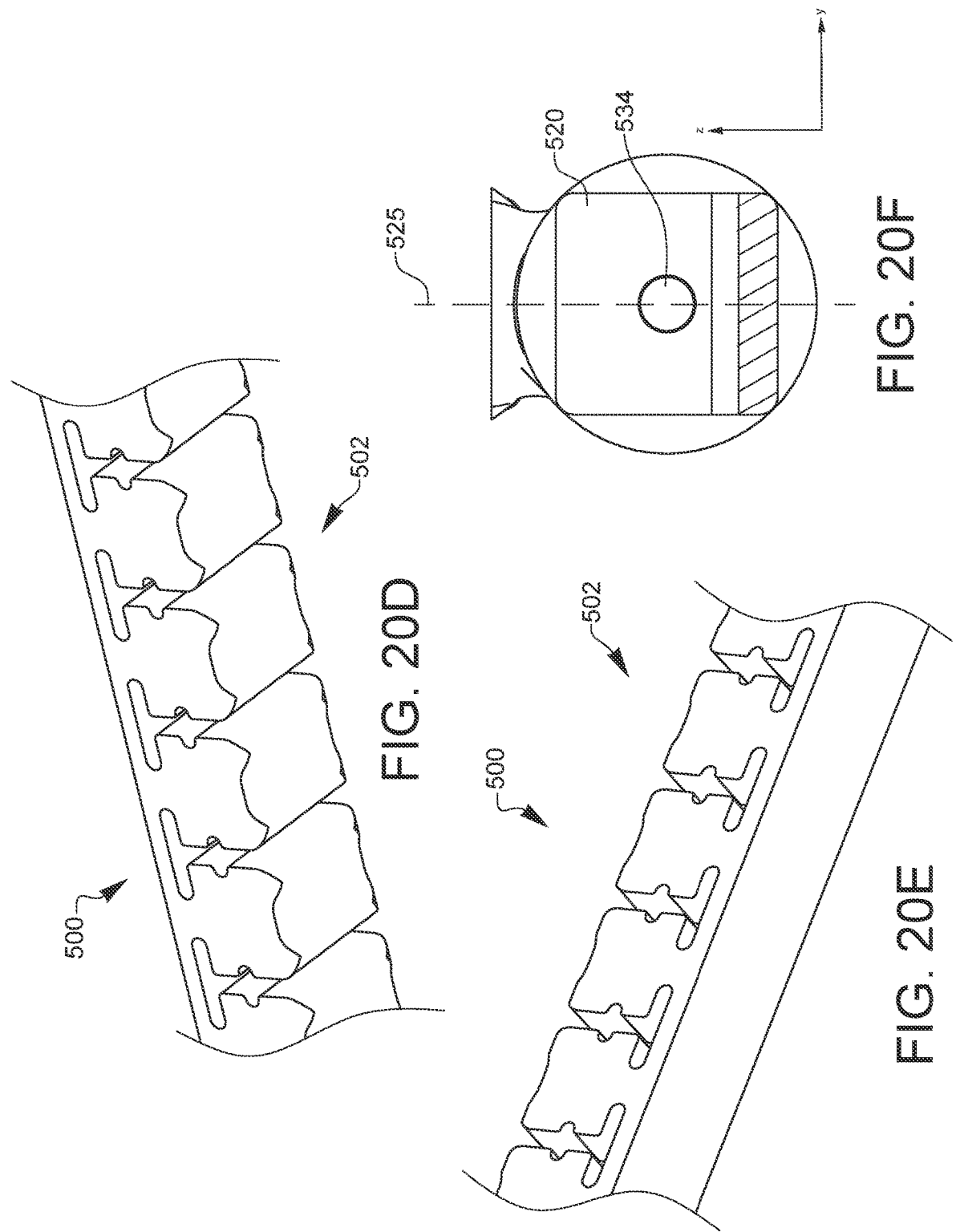

TISSUE MANIPULATION DEVICE

CROSS-REFERENCE TO RELATED APPLICATIONS

This application claims the benefit of U.S. Provisional Patent Application No. 63/245,310, filed Sep. 17, 2021, and U.S. Provisional Patent Application No. 63/335,937, filed Apr. 28, 2022, each of which is incorporated by reference herein in its entirety.

FIELD

The claimed invention relates to surgical devices, and more specifically to a tissue manipulation device.

BACKGROUND

A prostatectomy is a medical procedure to surgically remove the prostate gland of a male patient. The procedure is often performed due to disease of the prostate, such as cancer. The procedure may be performed by open surgery or laparoscopically by the use of endoscopic instruments through small incisions in the patient. In brief, the prostate is located along the urethra leading to the bladder, and removal of the prostate is performed by exposing the prostate, dissecting the tissue surrounding the prostate, removing the prostate, and then suturing the urethra to the bladder. One problem often encountered during a prostatectomy is that the prostate is difficult to position and maneuver by the surgeon to expose the tissue and place the tissue under tension during dissection to extract the gland. This is especially a problem with a laparoscopic prostatectomy. Another problem is that the neurovascular bundles adjacent the prostate can be damaged during the prostatectomy negatively effecting normal penile functionality. Precise dissection is important to minimize damage to surrounding tissue and especially the neurovascular bundles. Therefore, it would be desirable to provide an instrument which can be inserted through the urethra to engage the prostate and then enable the prostate's position to be precisely manipulated during a prostatectomy. It would also be desirable to provide a device that may be simple to disassemble for post-procedure cleaning and sterilization.

BRIEF DESCRIPTION OF THE DRAWINGS

FIG. 4A is a cross-sectional view of the embodiment of the tissue manipulation device of FIG. 1 with the securing member in an engaged position and in a first securing member position;

FIG. 4B is a cross-sectional view of the embodiment of the tissue manipulation device of FIG. 1 with the securing member in an engaged position and in a second securing member position;

FIG. 9A is a front view of an embodiment of the securing member;

FIG. 9B is a front view of the embodiment of the securing member of FIG. 9A;

FIG. 9C is a perspective view of the embodiment of the securing member of FIG. 9A;

FIG. 10A is a top view of the embodiment of the tissue manipulation device of FIG. 1;

FIG. 10B is a side view of the embodiment of the tissue manipulation device of FIG. 10A;

FIG. 10C is a bottom view of the embodiment of the tissue manipulation device of FIG. 10A;

FIG. 14A is a rear view of an embodiment of the tissue manipulation device coupled to an embodiment of a first robotic interface;

FIG. 14B is a rear view of an embodiment of the tissue manipulation device coupled to an embodiment of a first robotic interface;

FIG. 14C is a rear view of an embodiment of the tissue manipulation device coupled to an embodiment of a first robotic interface;

FIG. 17A is a side view of a portion of the torque member of the removable portion of the embodiment of the tissue manipulation device of FIG. 16;

FIG. 17B is a partial perspective view of the torque member of the removable portion of the embodiment of the tissue manipulation device of FIG. 20A;

FIG. 17C is a cross-sectional view of the embodiment of the torque member taken along section line 17C-17C in FIG. 17A;

FIG. 17D is top view of a portion of the torque member of the removable portion of the embodiment of the tissue manipulation device of FIG. 16;

FIG. 17E is a cross-sectional view of the embodiment of the torque member taken along section line 17E-17E in FIG. 17A;

FIG. 18A is a cross-sectional view of a portion of the shaft portion of an embodiment of the tissue manipulation device, and the cross-sectional view is taken along the shaft axis;

FIG. 18B is a cross-sectional view of a portion of the shaft portion of an embodiment of the tissue manipulation device, and the cross-sectional view is taken along section line 18B-18B in FIG. 18A;

FIG. 18C includes various cross-sectional views of a portion of the shaft portion of an embodiment of the tissue manipulation device, and the cross-sectional view is taken normal to the shaft axis adjacent to a distal end of a linear portion of the shaft portion;

FIG. 18D is a cross-sectional view of a portion of the shaft portion of an embodiment of the tissue manipulation device, and the cross-sectional view is taken along the shaft axis;

FIG. 19C is a cross-sectional view of the embodiment of the torque member taken along section line 19C-19C in FIG. 19D;

FIG. 19D is side view of a portion of the torque member of the removable portion of the embodiment of the tissue manipulation device of FIG. 19A;

FIGS. 20D and 20E are various perspective views of the torque member of the removable portion of the embodiment of the tissue manipulation device of FIG. 20A; and FIG. 20F is a cross-sectional view of the embodiment of the torque member taken along section line 20F-20F in FIG. 20C.

DETAILED DESCRIPTION

Figure 1:
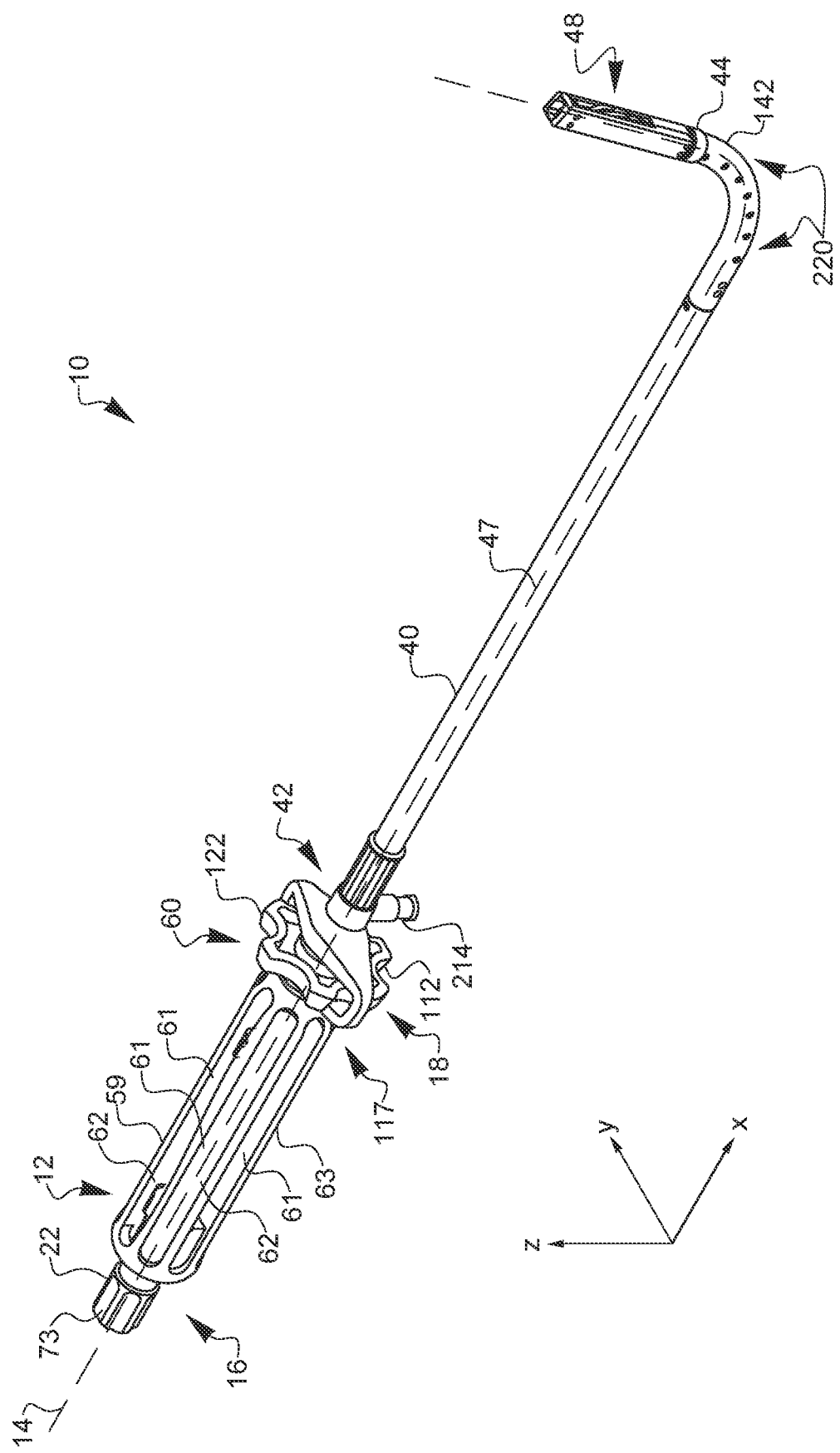
FIG. 1 is a perspective view of an embodiment of the tissue manipulation device.

Referring to FIG. 1, a tissue manipulation device 10 includes a handle portion 12 extending along a longitudinal axis 14 from a proximal end 16 to a distal end 18, and an adjustment member 22 is displaceably coupled to the proximal end 16 of the handle portion 12. As illustrated in the cross-sectional view of FIG. 3, a securing member 24 is coupled to the handle portion 12 and the securing member 24 extends along a member axis 26 from a proximal end 28 to a distal end 29. The securing member 24 includes an engagement portion 31 disposed at or adjacent to the distal end 29 of the securing member 24, and the proximal end 28 of the securing member 24 is coupled to a portion of the adjustment member 22 such that the securing member 24 is displaceable along the member axis 26 between a first securing member position 133 (illustrated in FIG. 4A) and a second securing member position (illustrated in FIG. 4B). In addition, the securing member 24 is pivotably coupled to the handle portion 12 and is pivotably displaceable from between an engaged position 36 (illustrated in FIG. 4A) and a disengaged position 39 (illustrated in FIG. 5). In the engaged position 36, the member axis 26 is parallel to or coaxially aligned with the longitudinal axis 14, and in the disengaged position 39, the member axis 26 is not parallel to or coaxially aligned with the longitudinal axis 14.

Referring again to FIG. 1, the tissue manipulation device 10 also includes a shaft portion 40 extending from a proximal end 42 to a distal end 44 along a shaft axis 47 (illustrated in FIG. 10A), and the proximal end 42 of the shaft portion 40 is coupled to the distal end of the handle portion 12. The tissue manipulation device 10 further includes an end effector 48 removably coupled to the distal end 44 of the shaft portion 40, and the end effector is operable between a first undeployed position 49 (illustrated in FIGS. 1 and 6) and a second deployed position 51 (illustrated in FIG. 8).

Figure 3:
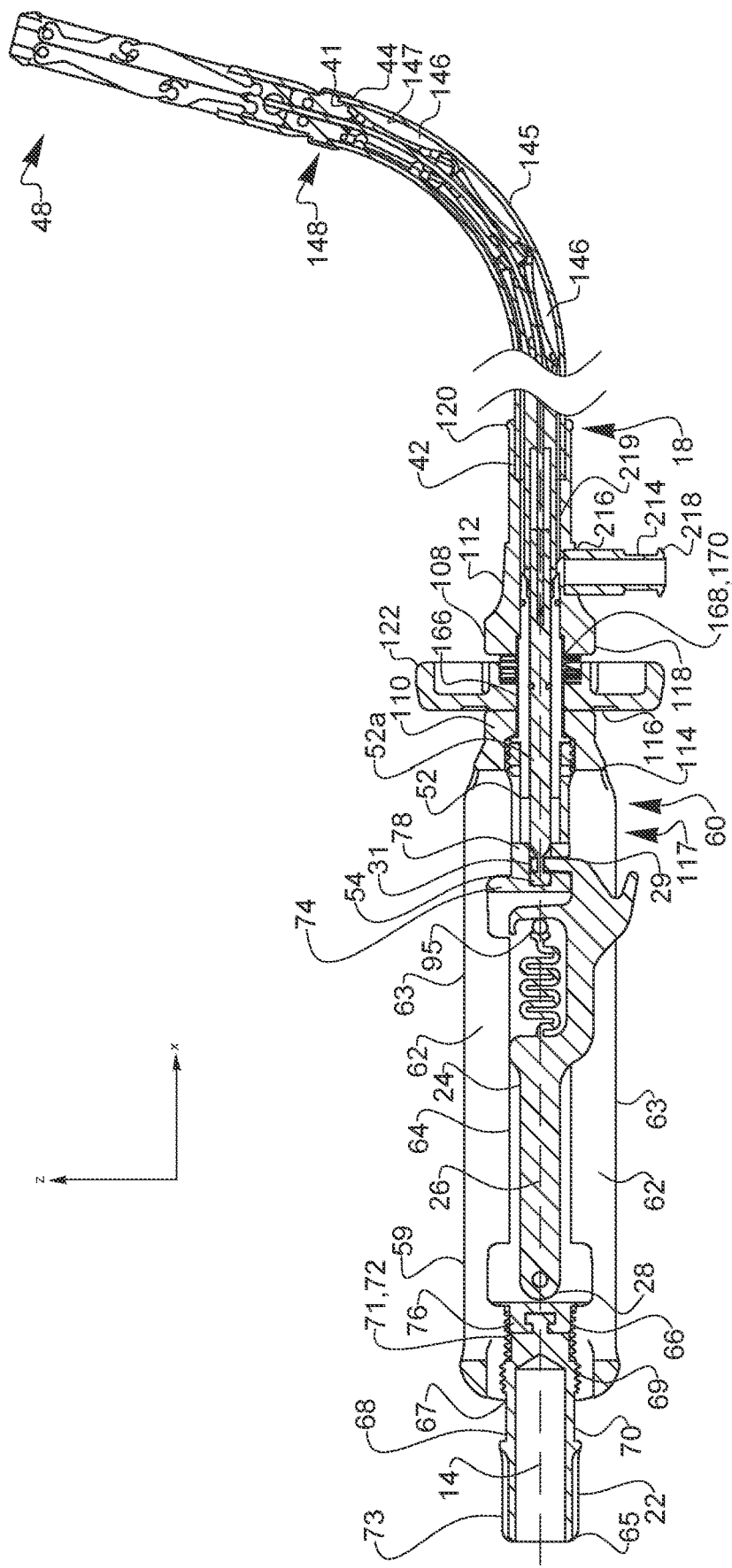
FIG. 3 is a cross-sectional view of the embodiment of the tissue manipulation device of FIG. 1 with a securing member in an engaged position.

With reference to FIG. 3, the tissue manipulation device 10 additionally includes a wire 52 (e.g., a flexible wire 52) extending from a proximal end 54 to a distal end 56 (illustrated in FIG. 8), and the distal end 56 of the wire 52 is coupled to the end effector 48. The proximal end 54 of the wire 52 is removably coupled to the engagement portion 31 of the securing member 24 when the securing member 24 is in the engaged position 36 (illustrated in FIG. 4A) and the proximal end 54 of the wire is disengaged from the engagement portion 31 of the securing member 24 when the securing member 24 is in the disengaged position 39 (illustrated in FIG. 5). In addition, when the securing member 24 is in the engaged position 36 (illustrated in FIG. 4A), the wire 52 couples the securing member 24 and the end effector 48 such that (a) when the securing member 24 is displaced from the first securing member position 133 (illustrated in FIG. 4A) to the second securing member position 35 (illustrated in FIG. 4B), the end effector 48 is displaced from the first undeployed position 49 (illustrated in FIGS. 1 and 6) to the second deployed position 51 (illustrated in FIG. 8) and (b) when the securing member 24 is displaced from the second securing member position 35 (illustrated in FIG. 4B) to the first securing member position (illustrated in FIG. 4A), the end effector 48 is displaced from the second deployed position 51 (illustrated in FIG. 8) to the first undeployed position 49 (illustrated in FIGS. 1 and 6).

So configured, when the securing member 24 is in the disengaged position 39, the end effector 48 may be decoupled from the distal end 44 of the shaft portion 40 and the wire 52 is configured to be removed from the shaft portion 40 through an aperture 41 (illustrated in FIG. 3) defined at the distal end 44 of the shaft portion 40. Accordingly, the wire 52 and attached end effector 48 may at least partially define a removable portion 57 (illustrated in FIG. 7) that may be separated and removed from the handle portion 12 and shaft portion 40 to allow the for separate processing (e.g., washing and sterilization) of the handle portion 12 and shaft portion 40. The removable portion 57 may also be processed separately from, or instead of, the handle portion 12 and shaft portion 40. In some embodiments, the removable portion 57 may further include one or more components may be coupled to the wire 52 and/or the end effector 58, such as one or more torque links 58 illustrated in FIG. 7.

Figure 2:
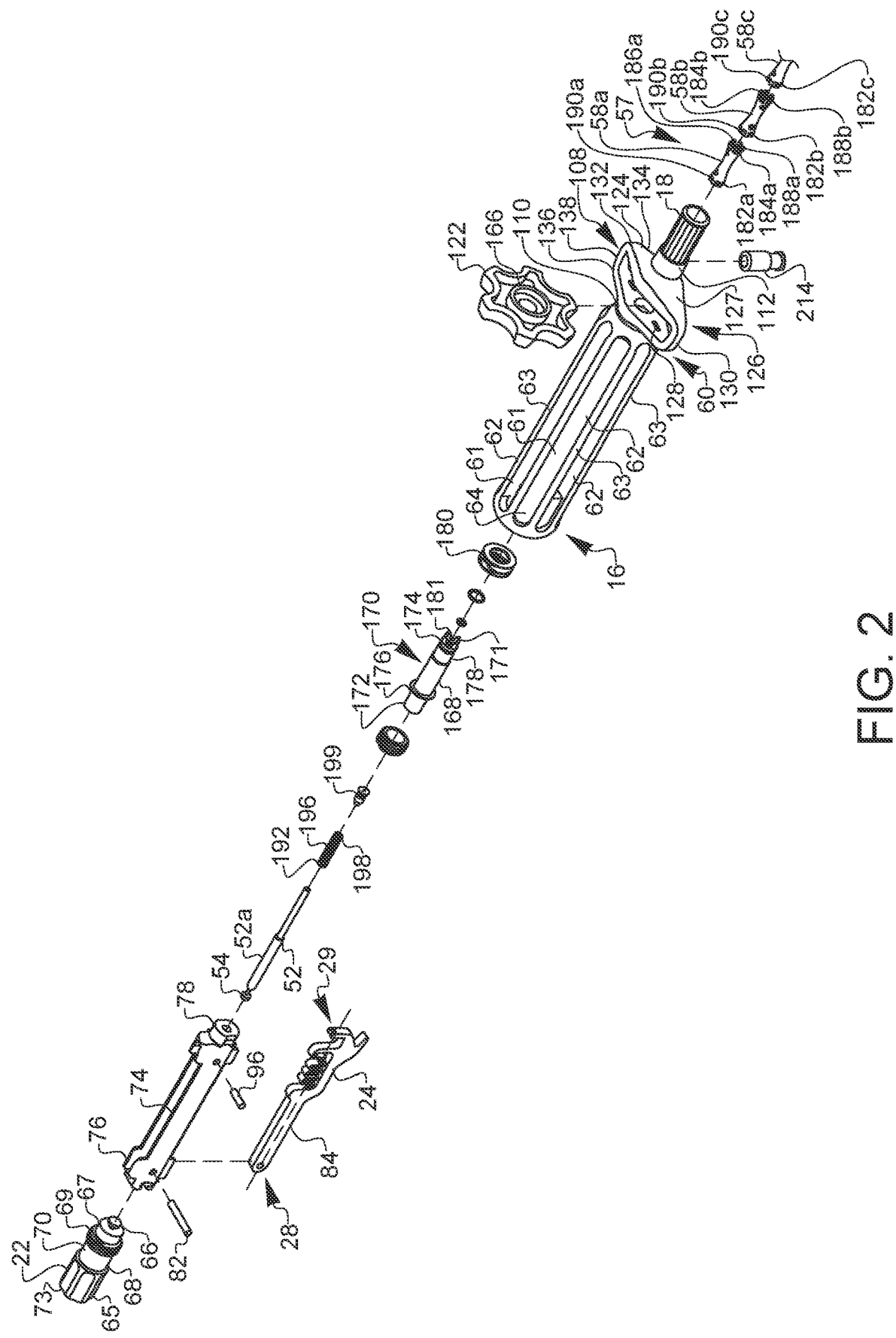
FIG. 2 is an exploded view of a portion of the embodiment of the tissue manipulation device of FIG. 1.

Turning to the tissue manipulation device 10 in more detail, and with reference to FIGS. 1, 2, and 3, the handle portion 12 may extend along the longitudinal axis 14 from the proximal end 16 to the distal end 18 and may include a grip portion 59 that may extend along the longitudinal axis 14 from the proximal end 16 of the handle portion 12 to a distal end 117 of the grip portion 59 at a first intermediary point 60 of the handle portion 12 that is proximal to the distal end 18 of the handle portion 12. The grip portion 59 may be shaped and dimensioned to be grasped by the hand of a user during a procedure. The grip portion 59 may include a plurality of slots 61 that each extends parallel to the longitudinal axis 14 from a point at or distal to the proximal end 16 of the handle portion 12 to a point at or proximal to the first intermediary point 60 of the handle portion 12. The plurality of slots 61 may be radially arrayed about the longitudinal axis 14, and the plurality of slots 61 may cooperate to define a plurality of ridges 62. Correspondingly, the plurality of ridges 62 may be radially arrayed about the longitudinal axis 14, and each of the plurality of ridges 62 may extend parallel to the longitudinal axis 14 from a point at or distal to the proximal end 16 of the handle portion 12 to a point at or proximal to the first intermediary point 60 of the handle portion 12. An outer end surface 63 of each of the plurality of ridges 62 may be contoured or textured to comfortably and securely be grasped by the hand of a user during a procedure.

Referring to FIGS. 2 and 3, the handle portion 12 may further include a central bore 64 that may extend along the longitudinal axis 14 from the proximal end 16 of the handle portion 12 to the first intermediary point 60 of the handle portion 12 or to a point distal to the first intermediary point 60 of the handle portion 12. The central bore 64 may include an end portion 71 and a portion of the end portion 71 may include a threaded portion 72.

Referring to FIGS. 1 to 3, the tissue manipulation device 10 may further include the adjustment member 22 which is displaceably coupled to the proximal end 16 of the handle portion 12. With reference to FIGS. 2 and 3, the adjustment member 22 may extend along the longitudinal axis 14 from a proximal end 65 to a distal end 66, and an insertion portion 67 may extend from the distal end 66 to an intermediary point 68. An input portion 73 may extend proximally from the insertion portion 67, and the input portion 73 may extend from the intermediary point 68 to the proximal end 65 of the adjustment member 22. The insertion portion 67 may be at least partially received in the end portion 65 of the central bore 64 of the handle portion 12, and a threaded portion 69 of an outer surface 70 of the insertion portion 67 may threadedly engage the threaded portion 72 of the end portion 65 of the central bore 64 of the handle portion 12. Accordingly, when a user rotates the input portion 73 (relative to the handle portion 12) about the longitudinal axis 14 in a first rotational direction, the adjustment member 22 displaces distally along the longitudinal axis 14. Correspondingly, when the user rotates the input portion 73 (relative to the handle portion 12) about the longitudinal axis 14 in a second rotational direction, the adjustment member 22 displaces proximally along the longitudinal axis 14.

As illustrated in the exploded view of FIG. 2, the tissue manipulation device 10 may include the securing member carrier 74 that may extend from a proximal end 76 to a distal end 78 along an axis that may be along or parallel to the longitudinal axis 14. The securing member carrier 74 may include a pair of opposing side walls 80a, 80b that may have corresponding inner surfaces that are planar or substantially planar. A pivot post 82 may extend between, and may be fixed relative to, the pair of inner surfaces of the pair of opposing side walls 80a, 80b, and the pivot post 82 may extend in a direction that is transverse to the longitudinal axis 14. The pivot post 82 may be disposed at any suitable location on the securing member carrier 74, such as at or adjacent to the proximal end 76 of the securing member carrier 74, for example.

The securing member carrier 74 may be displaceably disposed in any suitable portion of the central bore 64 of the handle portion 12. For example, as illustrated in the cross-sectional view of FIG. 3, the proximal end 76 of the securing member carrier 74 may be distal to the to the proximal end 16 of the handle portion 12 and the distal end 78 of the securing member carrier 74 may be proximal to the to the distal end 18 of the handle portion 12. In some embodiments, a portion of the proximal end 76 of the securing member carrier 74 may be coupled to or in contact with a portion of the adjustment member 22 that is at or adjacent to the distal end 66 of the adjustment member 22 such that a displacement of the adjustment member 22 along the longitudinal axis 14 for a first distance in a distal direction will result in a corresponding displacement of the securing member carrier 74 along the longitudinal axis 14 for the first distance in the distal direction. Similarly, a displacement of the adjustment member 22 along the longitudinal axis 14 for a second distance in a proximal direction will result in a corresponding displacement of the securing member carrier 74 along the longitudinal axis 14 for the second distance in the proximal direction.

As illustrated in FIGS. 2, 3, and 9A, the tissue manipulation device 10 may include the securing member 24 that may extend along the member axis 26 from the proximal end 28 to the distal end 29. Referring to FIGS. 9A and 9B, the securing member 24 may be planar or substantially planar, and may be at least partially defined by a first side surface 84a and a second side surface 84b opposite to the first side surface 84a. The first side surface 84a and the second side surface 84b may be separated by a constant width, and the width may be less than the distance separating the pair of inner surfaces of the pair of opposing side walls 80a, 80b of the securing member carrier 74 (illustrated in FIG. 2) such that all or a portion of the securing member 24 may be disposed between the pair of inner surfaces of the pair of opposing side walls 80a, 80b of the securing member carrier 74 when the securing member 24 is in the engaged position 36 (illustrated in FIG. 4A).

Still referring to FIG. 9A, the securing member 24 may include a shaft portion 86 that may extend along the member axis 26 from the proximal end 28 of the securing member 24 to an intermediate point 88. A lateral portion 90 may extend distally from the shaft portion 86, and may extend along an axis that is parallel to and offset from the member axis 26 from a point aligned with the intermediate point 88 to a point at or adjacent to the distal end 29 of the securing member 24. A support arm 92 may extend from a distal portion of the lateral portion 90 that is at or adjacent to the distal end 29 of the securing member 24. In particular, the support arm 92 may extend inwardly (i.e., towards the member axis 26) from a portion of an inner lateral edge 102 of the lateral portion 90 that is proximal to the distal end 29 of the securing member 24. The support arm 92 may extend along an axis that is transverse (or substantially transverse) to the member axis 26. The engagement portion 31 that is adapted to couple to the proximal end 54 of the wire 52 (as illustrated in FIG. 3) may be disposed on a portion of the support arm 92, such as a portion at or adjacent to an end portion of the support arm 92. The engagement portion 31 may be any feature that may removably coupled to the proximal end 54 of the wire 52, such as a slot or a yoke feature. In other embodiments, such as embodiments not having a support arm 92, the engagement portion 31 may be disposed at any suitable portion of the securing member 24, such as a portion of the securing member 24 that is at or adjacent to the distal end 29 of the securing member 24.

The securing member 24 may also include a stop arm 94 that may extend from a portion of the lateral portion 90 that is proximal to the distal end 29 of the securing member 24. In particular, the stop arm 94 may extend inwardly extend from a portion of the inner lateral edge 102 of the lateral portion 90 that is proximal to the distal end 29 of the securing member 24. The stop arm 94 may extend along an axis that is transverse (or substantially transverse) to the member axis 26, and this axis may be parallel or substantially parallel to the axis of the support arm 92 such that the stop arm 94 is proximally offset from the axis of the support arm 92 (e.g., offset in direction extending along the member axis 26 towards the proximal end 28 of the securing member 24). The stop arm 94 may be positioned on the securing member 24 such that a portion of a lower surface of the stop arm 94 may contact a portion of a stop post 96 (illustrated in FIG. 3) when the securing member 24 is in the first securing member position (illustrated in FIG. 4A) to prevent further proximal displacement of the securing member 24. The stop post 96 may extend in a direction that is transverse to the longitudinal axis 14 (and parallel to the pivot post 82), and the stop post may be fixedly coupled to a portion of the handle portion 12 in any suitable location to allow for the contact between the portion of the lower surface of the stop arm 94 and the portion of the stop post 96 when the securing member 24 is in the first securing member position (illustrated in FIG. 4A) The stop arm may have a curved end 95 that may be configured to contact the stop post 96 to prevent further pivoting of the securing member 24 relative to the handle member 12.

The securing member 24 may additionally include a resilient member 98 that may be coupled to or integrally formed with the securing member 24. For example, the resilient member 98 may be spring that extends along (or parallel to) the member axis 26 and may expand and retract along (or parallel to) the member axis 26. The resilient member 98 may include a plurality of parallel portions disposed transverse to the member axis 26, and ends of the parallel portions are coupled by alternating curved portions. A first end portion 99 of the resilient member 98 may be configured to be in contact with the stop post 96 when the securing member 24 is in the engaged position 36 (illustrated in FIG. 4A) and the first end portion 99 of the resilient member 98 may be configured to not contact the stop post 96 when the securing member 24 is pivoted to the disengaged position 39 (illustrated in FIG. 5). While the resilient member 98 has been described as integrally formed with the securing member 24, in some embodiments, the resilient member 98 may be coupled to any suitable portion of the securing member 24.

The securing member 24 may be pivotably or rotatably coupled to the securing member carrier 74 in any suitable manner. For example, a pivot aperture 100 may be disposed in a portion of the securing member 24 at or adjacent to the proximal end 28 of the securing member 24, such as a portion of the shaft portion 86 that is at or adjacent to the proximal end 28 of the securing member 24. The pivot post 82 of the securing member carrier 74 may be disposed through the pivot aperture 100 such that the securing member 24 is pivotably displaceable about the pivot post 82 between the engaged position 36 (illustrated in FIG. 4A) and the disengaged position 39 (illustrated in FIG. 5). The securing member 24 may be pivoted (for example, about the pivot post 82) to any suitable degree such that the engagement portion 31 of the securing member 24 may be disengaged or decoupled from the proximal end 54 of the wire 52. As such, when in the disengaged position 39, the member axis 26 of the securing member 24 may form an angle between 1 degree and 180 degrees with the longitudinal axis 14 to allow the engagement portion 31 of the securing member 24 to disengage or decouple from the proximal end 54 of the wire 52.

Because the securing member 24 is fixedly coupled to the securing member carrier 74 by the pivot post 82 in the engaged position 36, the securing member 24 may translate with the securing member carrier 74 along the longitudinal axis 14 when the securing member carrier 74 is longitudinally displaced by the adjustment member 22, as previously described. In addition, because the first end portion 99 of the resilient member 98 of the securing member 24 is in contact with the stop post 96 coupled to the handle portion 12, the proximal end 76 of the securing member carrier 74 is biased into engagement with the distal end 66 of the adjustment member 22. The resilient member 98 also biases the engagement portion 31 of the securing member 24 (which is coupled to the proximal end 54 of the wire 52) toward the proximal end 16 of the handle portion 12, which maintains tension in the wire 52.

The securing member 24 may also include a grip tab 104 that may facilitate the grasping of the securing member 24 by a user to pivot the securing member 24 from the engaged position 36 the disengaged position 39, and vice versa. The grip tab 104 may extend from a portion of the lateral portion 90 that is proximal to the distal end 29 of the securing member 24, and the grip tab 104 may extend outwardly from a portion of an outer lateral edge 106 of the lateral portion 90 that is proximal to the distal end 29 of the securing member 24.

Turning again to the handle portion 12 of the tissue manipulation device 10, FIG. 1 illustrates an embodiment in which the handle portion 12 includes a wheel housing portion 108 that is distal to the distal end 117 of the grip portion 59 and coupled to or integrally formed with the distal end 117 of the grip portion 59. With reference to FIG. 3, the wheel housing portion 108 may include a proximal support portion 110 and a distal support portion 112. The proximal support portion 110 may be cylindrical or substantially cylindrical and may extend along the longitudinal axis 14 from a proximal end 114 to a distal end 116. The proximal end 114 may be coupled to or integrally formed with the distal end 117 of the grip portion 59, and one or more interior surfaces of the proximal support portion 110 may cooperate to form a portion of the central bore 64 of the handle portion 12.

The distal support portion 112 may be distal to and longitudinally offset from the proximal support portion 110. The distal support portion 112 may be cylindrical or substantially cylindrical and may extend along the longitudinal axis 14 from a proximal end 118 to a distal end 120. In embodiments including the wheel housing portion 108, the distal end 120 of the distal support portion 112 may be disposed at or correspond to the distal end of the handle portion 12. One or more interior surfaces of the distal support portion 112 may cooperate to form a portion of the central bore 64 of the handle portion 12. An adjustment wheel 122 may be disposed in the space between the proximal end 118 of the distal support portion 112 and the distal end 116 of the proximal support portion 110, and the adjustment wheel 122 will be discussed in more detail below.

As illustrated in FIG. 2, a guard portion 124 may couple the proximal support portion 110 and the distal support portion 112. In particular, the guard portion 124 may include a first arm 126 having a first distal portion 127 extending from a portion of the distal support portion 112 along an axis that is substantially transverse to the longitudinal axis 14. The first arm 126 may also include a first proximal portion 128 extending from a portion of the proximal support portion 110 along an axis that is substantially transverse to the longitudinal axis. A first lateral portion 130 may extend between an end portion of the first distal portion 127 and an end portion of the first proximal portion 128.

The guard portion 124 may further include a second arm 132 having a second distal portion 134 extending from a portion of the distal support portion 112 along an axis that is substantially transverse to the longitudinal axis 14. The second arm 132 may also include a second proximal portion 136 extending from a portion of the proximal support portion 110 along an axis that is substantially transverse to the longitudinal axis 14. A second lateral portion 138 may extend between an end portion of the second distal portion 134 and an end portion of the second proximal portion 136. The second arm 132 may be symmetrical to the first arm 126 about a plane extending along the longitudinal axis 14. So configured, with the adjustment wheel 122 disposed in the space between the proximal end 118 of the distal support portion 112 and the distal end 116 of the proximal support portion 110, the first arm 126 and the second arm 132 of the guard portion 124 surround the adjustment wheel 122 to protect against unwanted rotation due to inadvertent contact with the adjustment wheel 122.

Referring now to FIG. 10A, the tissue manipulation device 10 also includes the shaft portion 40 extending from the proximal end 42 to the distal end 44 along the shaft axis 47. The proximal end 42 of the shaft portion 40 may be coupled to the distal end 18 of the handle portion 12. In embodiments including the wheel housing portion 108, the proximal end 42 of the shaft portion 40 may be coupled to the distal end 120 of the distal support portion 112 (illustrated in FIG. 3). However, the proximal end 42 of the shaft portion 40 may be coupled to any suitable portion of the shaft portion 40, such as the distal end 117 of the grip portion 59 (illustrated in FIG. 1) in embodiments that do not include the wheel housing portion 108. The distal end 44 of the shaft portion 40 may be removably coupled to a portion of the end effector 48.

The shaft portion 40 may have any suitable shape or combination of shapes. For example, the shaft portion 40 may include a linear portion 140 and a curved portion 142. The linear portion 140 may extend from the proximal end 42 of the shaft portion to an intermediate point 144 of the shaft portion 40. The portion of the shaft axis 47 that extends along the linear portion 140 may be aligned with the longitudinal axis 14 or may be parallel to the longitudinal axis 14. In some embodiments, the portion of the shaft axis 47 that extends along the linear portion 140 may form an angle (i.e., an acute angle) with the longitudinal axis 14. The curved portion 142 of the shaft portion 40 may extend from the intermediate point 144 of the shaft portion 40 to the distal end 44 of the shaft portion 40. In some embodiments, the curved portion 142 may be linear and the portion of the shaft axis 47 that extends along the curved portion 142 may form an angle (i.e., an acute angle) with the longitudinal axis 14 and/or with the portion of the shaft axis 47 that extends along the linear portion 140. In other embodiments, the shaft portion 40 may not have a curved portion 142 and the linear portion 140 may extend from the proximal end 42 of the shaft portion 40 to the distal end 44 of the shaft portion 40. In still further embodiments, the shaft portion 40 may not have a linear portion 140 and the curved portion 142 may extend from the proximal end 42 of the shaft portion 40 to the distal end 44 of the shaft portion 40.

As illustrated in FIG. 3, the shaft portion 40 may have one or more exterior surfaces 145 and may have one or more interior surfaces 147 that define a shaft interior portion 146. The shaft interior portion 146 may open into, be in communication, and/or be aligned with the central bore 64 of the handle portion 12. The one or more exterior surfaces 145 and one or more interior surfaces 147 may have any suitable cross-sectional shape of combination of shapes. For example, the one or more exterior surfaces 145 and/or the one or more interior surfaces 147 may have a circular (or polygonal) cross-sectional shape. The cross-sectional shape of any of the one or more exterior surfaces 145 and/or the one or more interior surfaces 147 may be uniform along the entire shaft portion 40 or along one or more segments of the shaft portion 40 (e.g., the linear portion 140).

With reference to FIG. 3, the tissue manipulation device 10 additionally includes the wire 52 that extends from the proximal end 54 to the distal end 56 (illustrated in FIG. 8), and the distal end 56 of the wire 52 may be coupled to a portion of the end effector 48, such as a proximal portion 148 of the end effector 48. All or a portion of the wire 52 may be flexible to allow the wire 52 to extend through the curved portion 142 of the shaft portion 40. The wire 52 may be a single unitary part or may be an assembly of two or more segments and/or components. For example, as illustrated in FIG. 3, the wire 52 may include a coupling portion 52a disposed at or adjacent to the proximal end 54 of the wire 52. As illustrated in FIG. 3, the proximal end 54 of the wire 52 may be removably coupled to the engagement portion 31 of the securing member 24 when the securing member 24 is in the engaged position 36 (illustrated in FIG. 4A), and the proximal end 54 of the wire 52 may be shaped or dimensioned to be removably engaged by the engagement portion 31 of the securing member 24.

Figure 8:
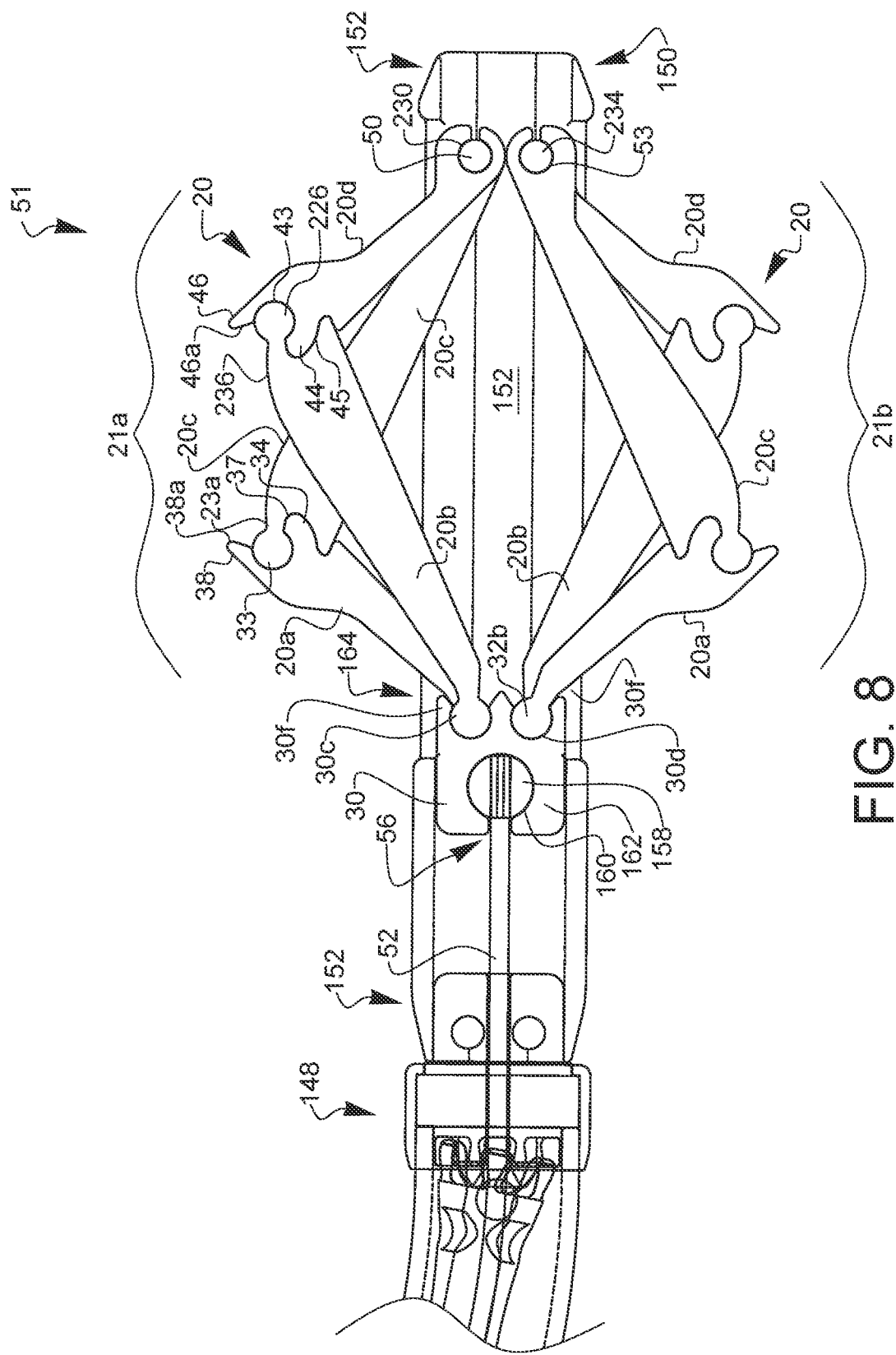
FIG. 8 is a cross-sectional view of the distal end of the shaft portion of the embodiment of the tissue manipulation device of FIG. 1 with the end effector in a second deployed position.

As illustrated in FIGS. 1, the tissue manipulation device 10 additionally includes the end effector 48 removably and rotatably coupled to the distal end 44 of the shaft portion 40, and the end effector is operable between a first undeployed position 49 (illustrated in FIGS. 1 and 6) and a second deployed position 51 (illustrated in FIG. 8). The distal end 56 of the wire 52 may be coupled to the proximal portion 148 of the end effector 48 such that when the securing member 24 is displaced (e.g., displaced distally in a direction along the member axis 26) from the first securing member position (illustrated in FIG. 4A) to the second securing member position 35 (illustrated in FIG. 4B), the end effector 48 is transitioned (e.g., expanded or deployed) from the first undeployed position 49 (illustrated in FIGS. 1 and 6) to the second deployed position 51 (illustrated in FIG. 8). Correspondingly, when the securing member 24 is displaced (e.g., displaced proximally in a direction along the member axis 26) from the second securing member position 35 (illustrated in FIG. 4B) to the first securing member position 133 (illustrated in FIG. 4A), the end effector 48 is transitioned (or contracted) from the second deployed position 51 (illustrated in FIG. 8) to the first undeployed position 49 (illustrated in FIGS. 1 and 6).

Turning to the end effector 48 in more detail, FIG. 10A illustrates an embodiment of the end effector 48 having a housing 150 that extends from a proximal end 151 to a distal end 152 along an end effector axis 153, and two windows 154a, 154b are formed on opposing lateral ends of the housing 150. As shown in the cross-sectional view of FIG. 8, the housing 150 includes a plurality of interior surfaces that cooperate to define a cavity 156 within the housing 150. In the cavity 152, disposed for extension through each of the windows 154*a*, 154*b*, is one of two sets 21*a* and 21*b* of two tissue engaging members 20. The tissue engaging members 20 are extendible from the first undeployed position 49 (illustrated in FIGS. 1 and 6) to the second deployed position 51 (illustrated in FIG. 8). In each of sets 21*a* and 21*b*, the first of the two tissue engaging members 20 is formed by a proximal member 20*a* and a distal member 20*c*, and the second of the two tissue engaging members 20 is formed by a proximal member 20*b* and a distal member 20*d*.

Each tissue engaging member 20 represents a hinged wing which is extendible radially through their respective windows 154*a*, 154*b* of the distal end. Turning to the first set 21*a*, proximal member 20*a* has a socket 33 which receives a curved member or shaft extending from the distal member 20*c* to form a hinge similar to a ball and socket joint. One side of the socket 33 extends to form a finger 34 which may be received in an opening 37 of distal member 20*c* shaped to receive finger 34. Proximal member 20*a* has a barb 38 which extends from the other side of the socket 33. Similarly, the proximal member 20*b* has a curved member or shaft 226 which is received in socket 43 of distal member 20*d* to form a hinge also similar to a ball and socket joint. One side of the socket 43 extends to form a finger 228 which may be received in an opening 45 of proximal member 20*b* shaped to receive finger 228. Proximal member 20*d* has a barb 46 which extends from the other side of socket 43. Proximal member 20*a* and distal member 20*d* may be of the same first length, and proximal member 20*b* and distal member 20*c* may be of the same second length, where the first length is less than the second length. The second set 21*b* is a mirror image of the first set 21*a*, and operates identically to the first set 21*a*.

In the first set 21*a*, a hole 230 is provided at the end 230 of distal member 20*c* through which extends a pin 50 through two openings in the sides of housing 150 near the distal end 152, and a hole is also provided at end of distal member 20*d* through which the pin 50 also extends. In the second set 21*b*, a pin 53 similarly extends through holes 233 through two openings in the sides of housing 150 near the distal end 152. Each of pins 50 and 53 are adjacent the one of windows 154*a*, 154*b* through which their respective tissue engaging member sets 21*a* and 21*b* are extendible and retractable.

As illustrated in FIG. 8, the end effector 48 also includes a plunger 30 disposed at least partially in the housing 150 at or adjacent to the distal end 152 of the housing 150, and the plunger 30 is longitudinally displaceable relative to the housing 150. In particular, a proximal end 158 of the plunger 30, which may correspond to (or be at or adjacent to) the proximal portion 148 of the end effector 48, may be coupled to the distal end 56 of the wire 52. The proximal end 158 of the plunger 30 may be coupled to the distal end 56 of the wire 52 in any suitable manner. For example, the distal end 56 of the wire 52 may include an enlarged portion 160 (such as a ball end) that is disposed within a cavity 162 formed in a portion of the plunger 30. Thus, a distal displacement of the distal end 56 of the wire 52 results in a distal displacement of the plunger 30 with respect to the housing 150, and a proximal displacement of the distal end 56 of the wire 52 results in a proximal displacement of the plunger 30 with respect to the housing 150. In addition, the enlarged portion 160 and the cavity 162 are shaped and dimensioned configured to allow the plunger 30 (and the entire housing 150) to rotate relative to the distal end 56 of the wire 52.

The plunger 30 additionally includes two plunger sockets 30*c*, 30*d* formed in a distal end 164 of the plunger 30. At end 49*a* opposite socket 33 of proximal member 20*a* forms a curved member or shaft 32*a*, and at end 49*b* opposite pin 42 of proximal member 20*b* forms a curved member or shaft 32*b*. For tissue engaging member set 21*a*, curved members 32*a* and 32*b* of proximal members 20*a* and 20*b*, respectively, are received beside each other in the plunger socket 30*c* and are rotatable therein. For tissue engaging member set 21*b*, curved members 32*a* and 32*b* of proximal members 20*a* and 20*b*, respectively, are received beside each other in the plunger socket 30*d* and are rotatable therein. The walls 30*f* forming the plunger sockets 30*c* and 30*d* extend upwards to form fingers with tapered ends. This facilitates insertion of curved members 32*a* and 32*b* in one of the plunger sockets 30*c* and 30*d* for respective tissue engaging member sets 21*a* and 21*b*, such that the curved members 32*a* and 32*b* may inserted or removed from these sockets only at an angle not achievable when the distal end is fully assembled, thereby preventing the curved members 32*a* and 32*b* from falling out of their respective sockets during normal operation.

Figure 6:
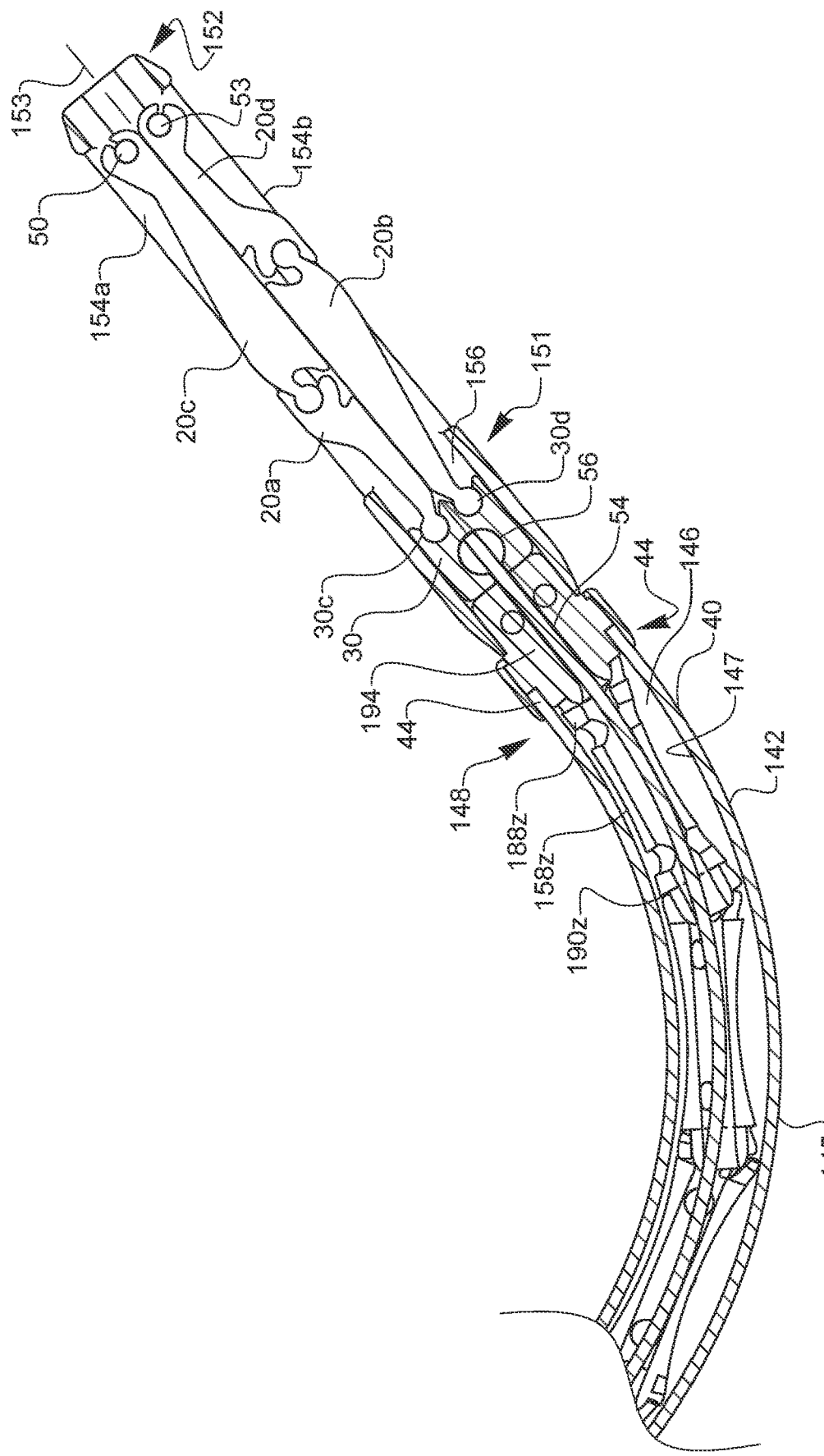
FIG. 6 is a cross-sectional view of a distal end of a shaft portion of the embodiment of the tissue manipulation device of FIG. 1 with the end effector in a first undeployed position.

As the plunger 30 moves distally in the housing 150 towards the distal end 152, the curved members 32*a* and 32*b* rotate in plunger socket 30*c* (for tissue engaging member set 21*a*) or 30*d* (for tissue engaging member set 21*b*), rotating curved members 36 and 42 of distal and proximal members 20*c* and 20*b*, respectively, in sockets 33 and 43 of proximal and distal members 20*a* and 20*d*, respectively, as distal members 20*c* and 20*d* rotate about pin 51 (for tissue engaging member set 21*a*) or 54 (for tissue engaging member set 21*b*), thereby extending outwards from the distal end 16 simultaneously both sets 21*a* and 21*b* of tissue engaging members 20. The degree of extension being controlled by the length of travel of the longitudinal drive mechanism and limited by fingers 34 and 44 of proximal and distal members 20*a* and 20*d*, respectively, being stopped by their full insertion into openings 37 and 45 of distal and proximal members 20*c* and 20*b*, respectively. As the plunger 30 moves towards the proximal end 151 of the housing 150, the above-described outward rotation of member 20*a-d* occur in the opposite direction, thereby retracting the tissue engaging members 20. The degree of retracting may be controlled by the length of travel of the plunger 30 and limited by the surface 38*a* of barb 38 of proximal member 20*a* abutting the surface 23*b* of distal member 20*c*, and the surface 46*a* of barb 46 of distal member 20*d* abutting the surface 25 of proximal member 20*b*. When fully retracted, the tissue engaging members 20 are substantially contained in the housing 150, and may extend slightly beyond the outer perimeter of the housing 150, as shown in FIG. 6.

Accordingly, when a user rotates the adjustment member 22 relative to the handle portion 12 such that the adjustment member 22 translates distally, the securing member carrier 74 also moves distally, thereby translating the securing member 24 from the first securing member position 133 (illustrated in FIG. 4A) to the second securing member position 35 (illustrated in FIG. 4B). As the securing member 24 displaces from the first securing member position 133 to the second securing member position 35, the distal end 56 of the wire 52 is displaced distally, thereby moving the plunger 30 distally within the housing 150 of the end effector 48, and the end effector 48 is displaced from the first undeployed position 49 (illustrated in FIGS. 1 and 6) to the second deployed position 51 (illustrated in FIG. 8).

Conversely, when a user rotates the adjustment member 22 relative to the handle portion 12 such that the adjustment member 22 translates proximally, the securing member carrier 74 also moves proximally (as illustrated in FIG. 4B, due to the bias caused by the first end portion 99 of the resilient member 98 of the securing member 24 that is in contact with the stop post 96), thereby translating the securing member 24 from the second securing member position 35 (illustrated in FIG. 4B) to the first securing member position 133 (illustrated in FIG. 4A). As the securing member 24 displaces from the second securing member position 35 to the first securing member position 133, the distal end 56 of the wire 52 is displaced proximally, thereby moving the plunger 30 proximally within the housing 150 of the end effector 48, and the end effector 48 is displaced from the second deployed position 51 (illustrated in FIG. 8) to the first undeployed position 49.

While the embodiment of the end effector 48 has been described as having two sets 21a, 21b of two tissue engaging members 20 that are extendible from the first undeployed position 49 to the second deployed position 51, other embodiments of the end effector are contemplated. In some of the other embodiments, the end effector 48 may be configured to extend, retract, or change position from a first position to a second position (and, optionally, further positions). In other embodiments, the end effector 48 may have a fixed configuration and not transition from a first position to a second position, In some embodiments, the end effector 48 may be rotatable relative to the shaft portion 40 during a procedure, providing the user with an advantageous additional rotational degree of freedom. In such embodiments, the adjustment wheel 122, which may be disposed in the space between the proximal end 118 of the distal support portion 112 and the distal end 116 of the proximal support portion 110, may be coupled to the end effector 48 to rotate the end effector 48 relative to the shaft portion 140.

In particular, as illustrated in FIG. 2, the adjustment wheel 122 may have a central aperture 166 that may be adapted to be disposed around an outer surface 168 of a wheel hub 170. The central aperture 166 may have a non-circular shape that may correspond to a non-circular shape of the outer surface 168 of the wheel hub 170 such that when the adjustment wheel 122 is rotated, the wheel hub 170 correspondingly rotates relative to the handle portion 12 (and the shaft portion 40). The wheel hub 170 may be elongated and may extend along a hub axis from a proximal end 172 to a distal end 174, and the hub axis may be aligned with the longitudinal axis 14. So configured, and as illustrated in FIG. 4B, all or a portion of a proximal portion 176 of the wheel hub 170 may be disposed through (and may be rotatable within) the proximal support portion 110 of the wheel housing portion 108 of the handle portion 12, and all or a portion of a distal portion 178 of the wheel hub 170 may be disposed through (and may be rotatable within) the distal support portion 112 of the wheel housing portion 108 of the handle portion 12. The wheel hub 170 may be maintained in proper longitudinal alignment by a plurality of Belleville springs 180 that are disposed between a proximal surface of the distal support portion 112 and a surface of the adjustment wheel 122, which is fixed to the wheel hub 170.

Still referring to FIG. 4B, the wheel hub 170 may have a central aperture 171 that extends through the wheel hub 170 from the proximal end 172 to the distal end 174 along the hub axis, and the central aperture 171 is in communication with the central bore 64 of the handle portion 12 As such, a portion of the wire 52 may be disposed through, and may displace longitudinally within, the central aperture 171 of the wheel hub 170. A plurality of gear teeth 182 may be disposed about a circumferential surface at the distal end 174 of the wheel hub 170 surrounding the central aperture 171, and the plurality of gear teeth 182 rotate about the longitudinal axis 14 as the adjustment wheel 122 is rotated.

Figure 7:
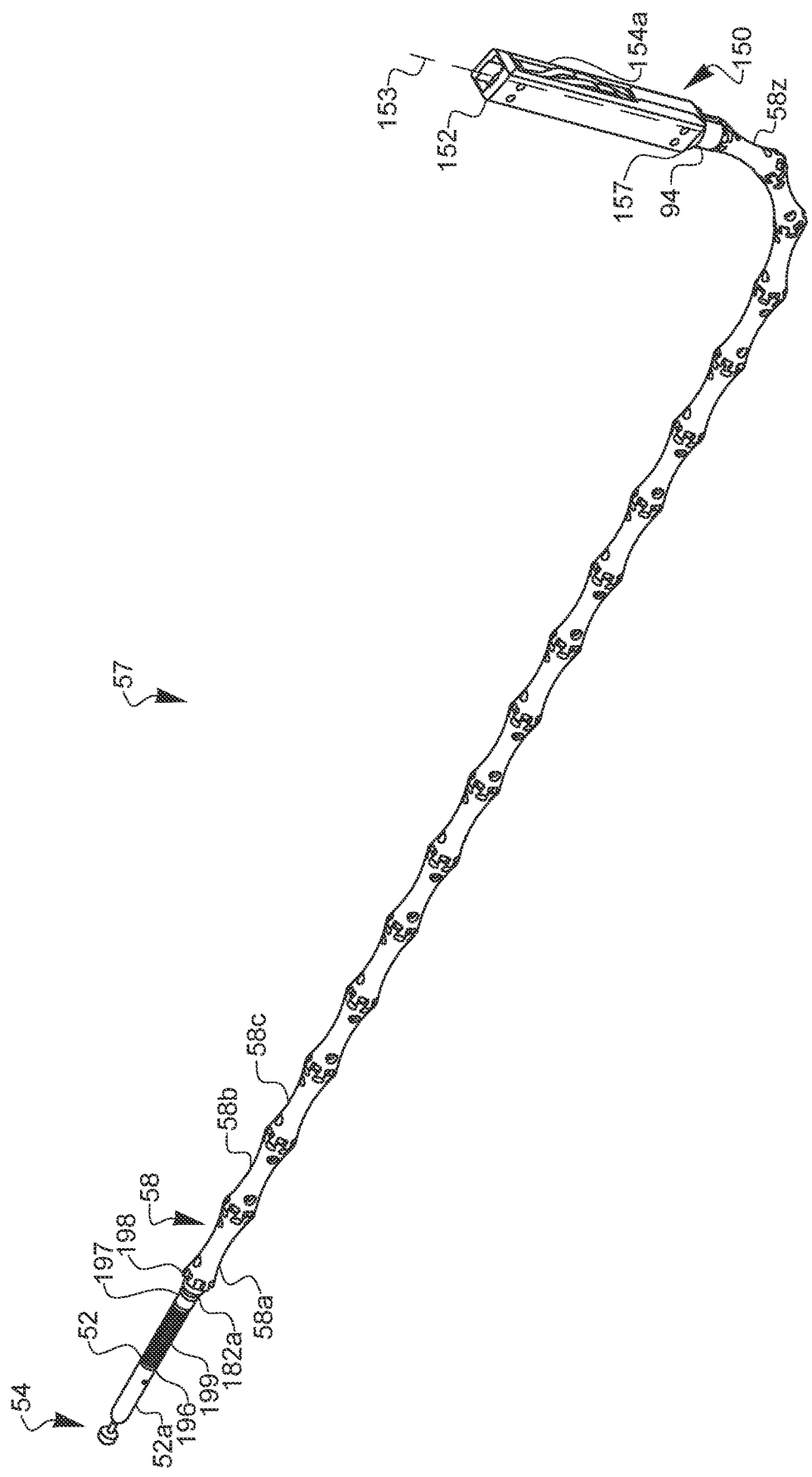
FIG. 7 is a perspective view of an embodiment of a removable assembly of the tissue manipulation device of FIG. 1.

Referring now to FIG. 7, the removable portion 57 of the tissue manipulation device 10 may include two or more torque links 58 that cooperate to rotatably couple the adjustment wheel 122 and the end effector 48. The two or more torque links 58 may include a first torque link 58a that may be rotatably coupled to the wheel hub 170. In particular, as illustrated in FIG. 2, the first torque link 58a may be elongated and may extend along an axis from a proximal end 182a to a distal end 184a, and a link bore 186a may extend through the first torque link 58a from the proximal end 182a to the distal end 184a. As such, a portion of the wire 52 may be disposed through, and may displace longitudinally within, the link bore 186a. A plurality of gear teeth 188a may be disposed about a circumferential surface at the distal end 184a of the first torque link 58a surrounding the link bore 186a. In addition, a plurality of receiving notches 190a may be disposed about a circumferential surface at the proximal end 182a of the first torque link 58a surrounding the link bore 186a. When the removable portion 57 is secured to the handle portion 12 and the shaft portion 40 of the tissue manipulation device 10, and when the securing member 24 is in the engaged position 36 (illustrated in FIG. 4A), each of the plurality of receiving notches 190a of the first torque link 58a may engage a corresponding one of the plurality of gear teeth 182 of the wheel hub 170 such that a rotation of the wheel hub 170 causes a corresponding rotation of the first torque link 58a.

Each of the two or more torque links 58 of the removable portion 57 may be identical. For example, the two or more torque links 58 may also include a second torque link 58b that may be identical to the first torque link 58a. That is, the second torque link 58b may be elongated and may extend along an axis from a proximal end 182b to a distal end 184b, and a link bore 186b may extend through the second torque link 58b from the proximal end 182b to the distal end 184b. As such, a portion of the wire 52 may be disposed through, and may displace longitudinally within, the link bore 186b. A plurality of gear teeth 188b may be disposed about a circumferential surface at the distal end 184b of the second torque link 58b surrounding the link bore 186b. In addition, a plurality of receiving notches 190b may be disposed about a circumferential surface at the proximal end 182b of the second torque link 58b surrounding the link bore 186b. When the removable portion 57 is secured to the handle portion 12 and the shaft portion 40 of the tissue manipulation device 10, and when the securing member 24 is in the engaged position 36 (illustrated in FIG. 4A), the second torque link 58b may be disposed distal to the first torque link 58a such that each of the plurality of gear teeth 188a of the first torque link 58a may engage a corresponding one of the plurality of receiving notches 190b of the second torque link 58b such that a rotation of the first torque link 58a causes a corresponding rotation of the second torque link 58b.

In some embodiments, the removable portion 57 may include any number of additional torque links 58, which may include the most distal torque link 58z. Distal torque link 58z may be identical to the first and second torque links 58a, 58b, and all other included torque links 58. As such, when the first torque link 58a is rotated by a corresponding rotation of the adjustment wheel 122, the second torque link 58b is also rotated as previously described, and the chain reaction of rotation would also rotate the distal torque link 58z. When the distal torque link 58z rotates, the gear teeth 188z of the distal torque link 58z also rotate, as would be understood by one having ordinary skill in the art. The gear teeth 188z of the distal torque link 58z engage corresponding receiving notches 192 on a proximal end of a connector portion 194 of the end effector 48. The connector portion 194 is fixedly coupled to the housing 150 of the end effector 48, and when the distal torque link 58z rotates from rotation of the adjustment wheel 122 as previously described, the end effector 40 also rotates relative to the shaft portion 40 about the end effector axis 153.

In some embodiments, the two or more torque links 58 include only two torque links, so the second torque link 58b corresponds to the distal torque link 58z. In other embodiments, the orientation of the on the gear teeth 188a and the receiving notches 190a previously described may be reversed. For example, the proximal end 182 of the first torque link 58a may have the gear teeth 188a and the distal end 184a of the first torque link 58a may include the receiving notches 190a, and all other torque links 58 and associated components may also be reversed. In other embodiments, the gear teeth 188a and the receiving notches 190a may be identical features such that the orientation of the torque links 58 along the wire 52 of the removable portion 57 does not matter.

As illustrated in FIG. 7, the removable portion 57 may include the two or more torque links 58 (for example, sixteen torque links 58), and a portion of the wire 52 may extend through the link bore 186 of each of the two or more torque links 58. In some embodiments, the removable portion 57 may also include a spring 196 that may surround a portion of the wire 52, and the spring may extend from a proximal end 197 to a distal end 198 along an axis aligned with the portion of the wire 52. The proximal end 197 of the spring 196 may be coupled to a portion of the wire 52 adjacent to the proximal end 54 of the wire 52, such as a distal end of the coupling portion 52a disposed at or adjacent to the proximal end 54 of the wire 52.

The distal end 198 of the spring 196 may be directly or indirectly coupled to the proximal end 182a of the first torque link 58a. In some embodiments, the distal end 198 of the spring 196 may be coupled to a proximal end of a cylindrical member 199, and the distal end of the cylindrical member 199 may be in contact with a portion of the proximal end 182a of the first torque link 58a. So positioned, the spring 195 operates to bias the first torque link 58a towards the distal end 56 of the wire 52, which biases the distal end 184a of the first torque link 58a into engagement with the proximal end 182b of the second torque link 58b, which similarly biases each of the remaining torque links 58 distally such that the gear teeth 188z at the distal end 184z of the distal torque link 58z is biased into engagement with the corresponding receiving notches 192 on the proximal end of the connector portion 194 of the end effector 48.

Accordingly, when the securing member 24 is pivoted from the engaged position 36 (illustrated in FIG. 4A) to the disengaged position 39 (illustrated in FIG. 5), the removable portion 57 may be removed from the shaft portion 40 and handle portion 12. In some embodiment, a locking mechanism (not shown), such as a pin extending through an aperture, may couple the end effector 48 to the distal end 44 of the shaft portion 40, and this locking mechanism should be disabled (e.g., by removing the pin) prior to removing the removable portion 57. Once the end effector 48 is no longer secured to the distal end 44 of the shaft portion 40, the end effector 48 may be grasped by a user and displaced along the end effector axis 153 away from the distal end 44 of the shaft portion 40 until a proximal end 200 of the removable portion 57, which may be the proximal end 54 of the wire 52, extends past the distal end 44 of the shaft portion 40. One having ordinary skill in the art would recognize that the removable portion 57 would be bendable between any two adjacent torque links 58, and this ability to bend allows the chain of torque links 58 allows the removable portion 57 to be passed through the curved portion 142 of the shaft portion 40 when inserting or removing the removable portion 57 for disassembly or reassembly.

Once the removable portion 57 has been removed from the handle portion 12 and shaft portion 40, the handle portion 12 and shaft portion 40 may undergo a process (e.g., washing and sterilization). Alternatively, the removable portion 57 may also be processed separately from, or instead of, the handle portion 12 and shaft portion 40. To reattach the removable portion 57, or to attach a new removable portion 57, the described steps are reversed.

Figure 11:
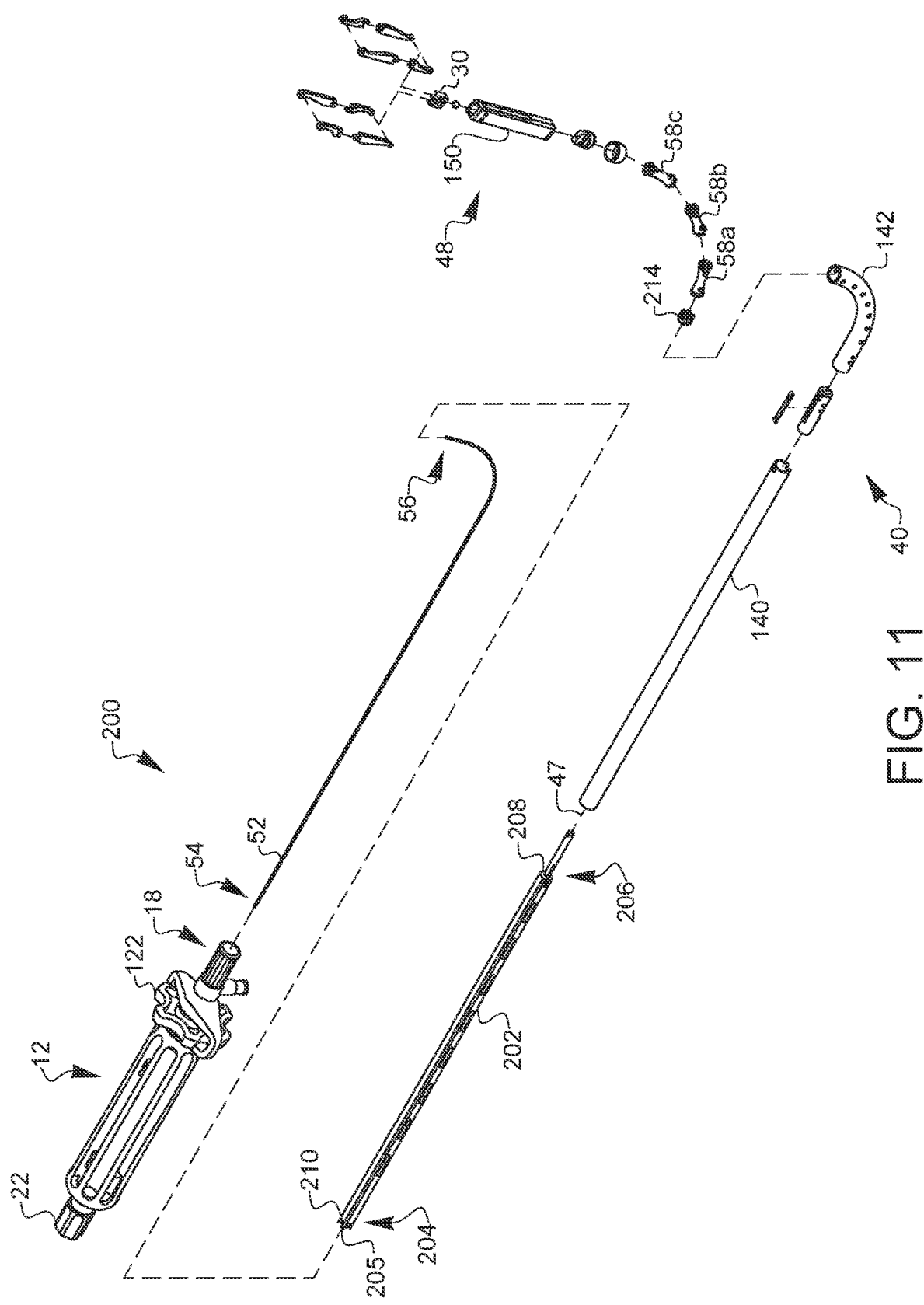
FIG. 11 is an exploded view of a portion of a further embodiment of the tissue manipulation device.
Figure 12:
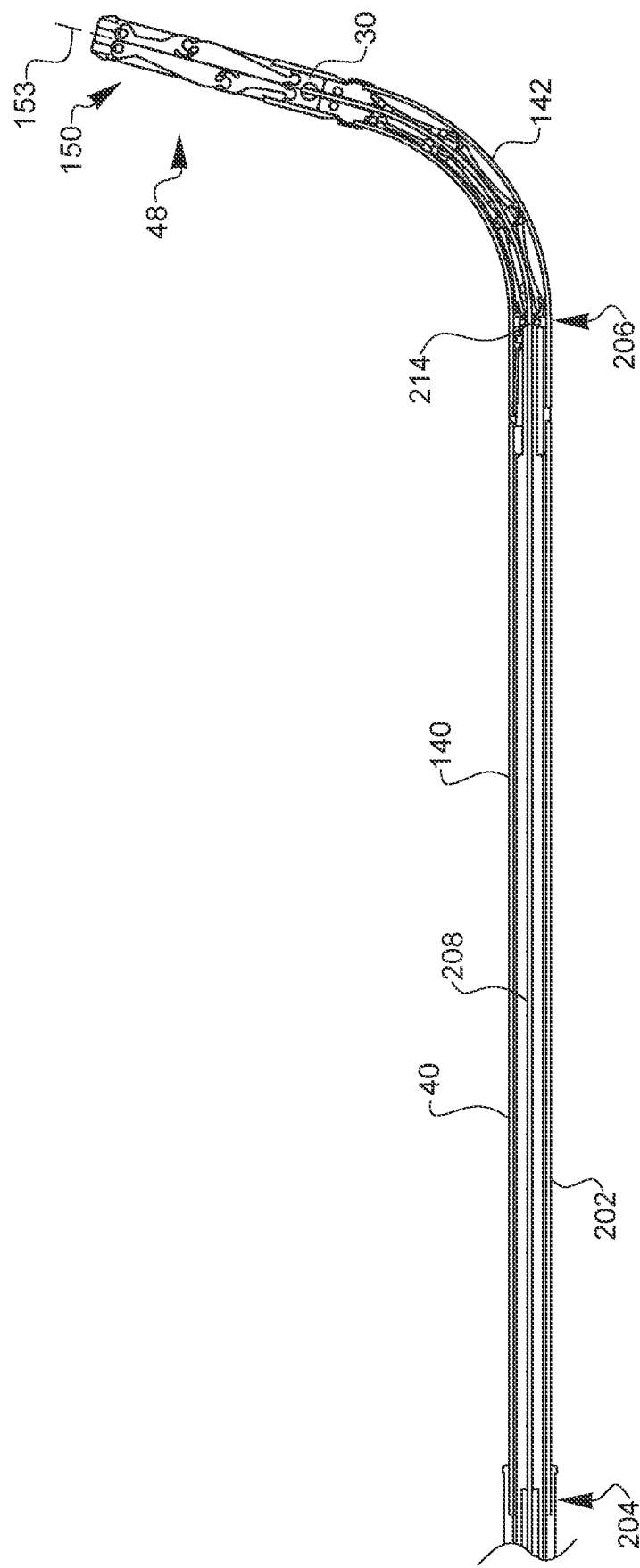
FIG. 12 is a cross-sectional view of a shaft portion of the embodiment of the tissue manipulation device of FIG. 11.
Figure 13:
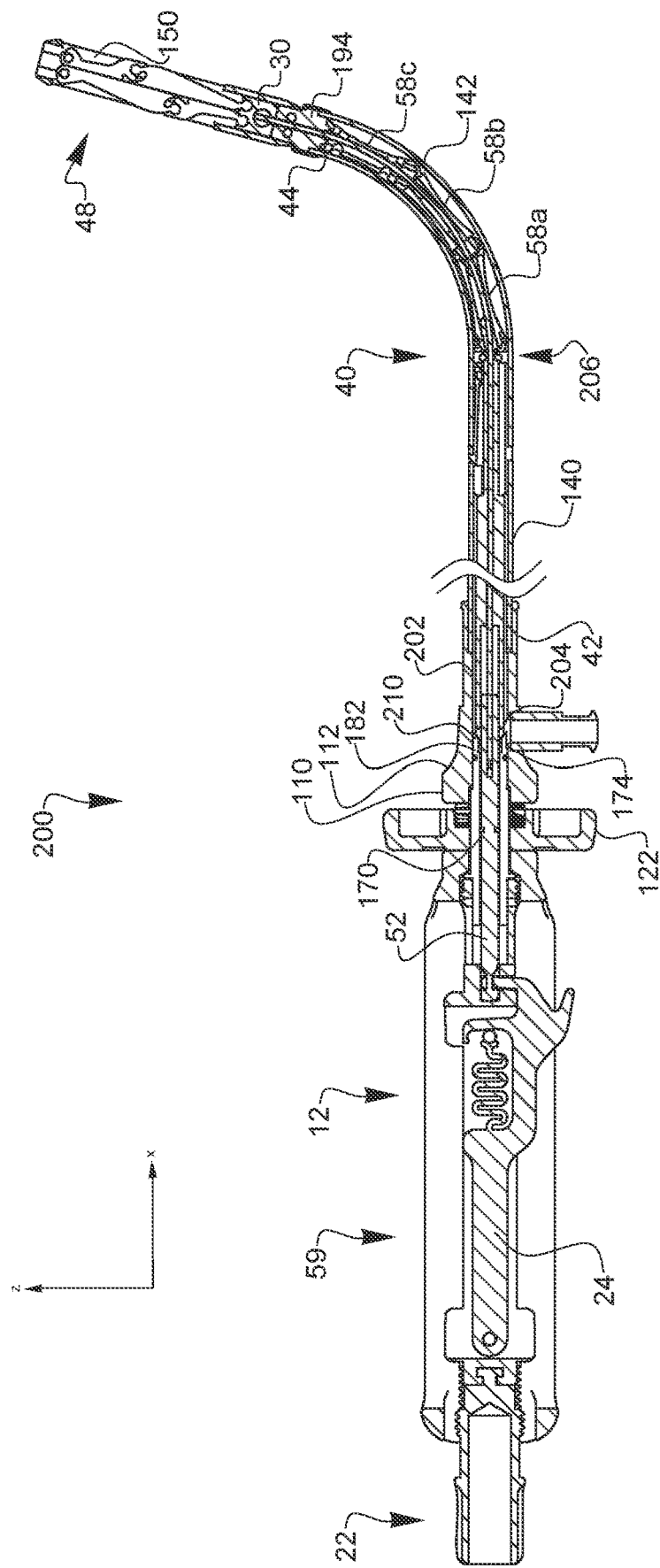
FIG. 13 is a cross-sectional view of the embodiment of the tissue manipulation device of FIG. 11.

Turning to a further embodiment illustrated in FIGS. 11 to 13, the tissue manipulation device 200 may be substantially identical to the tissue manipulation device 10 previously described, with the exception that a rigid torque member 202 may replace one or more of the torque links 58. In particular, the torque member 202 may extend along an axis 205 from a proximal end 204 to a distal end 206, and the axis 205 may be aligned with the portion of the shaft axis 47 that extends along the linear portion 140 of the shaft portion 40. The torque member 202 may include a central bore 208 that extends through the torque member 202 from the proximal end 204 to the distal end 206 along the axis 205. The torque member may have any suitable cross-sectional shape or combination of shapes to allow the torque member 202 to transmit torque and to fit in the linear portion 140 of the shaft portion 40.

The torque member 202 may be a single, unitary part or may be an assembly of two or more components that cooperate to form the torque member 202. In operation, a portion of the wire 52 may be disposed through, and be longitudinally displaceable within, the central bore 208 of the torque member 202. In some embodiments, a guide sheath (not shown) may surround all or a portion of the portion of the wire 52 that extends through the central bore 208 of the torque member 202.

A plurality of receiving notches 210 may be disposed about a circumferential surface at the proximal end 204 of the torque member 202 surrounding the central bore 208. When the securing member 24 is in the engaged position 36 (illustrated in FIG. 13), each of the plurality of receiving notches 210 of the torque member 202 may engage a corresponding one of the plurality of gear teeth 182 of the wheel hub 170 such that a rotation of the wheel hub 170 causes a corresponding rotation of the torque member 202 about the axis 205.

The torque member 202 may extend distally such that the distal end 206 of the torque member 202 is disposed at or adjacent to the intermediate point 144 of the shaft portion 140, which is at a distal end of the distal end of the linear portion 140 of the shaft portion 40 and at a proximal end of the of the curved portion 142 of the shaft portion 40. A plurality of gear teeth 212 may be disposed about a circumferential surface at the distal end 204 of the torque member 202 surrounding the central bore 208. The plurality of gear teeth 212 may be disposed on a removable end portion 214 that forms the distal end 206 of the torque member 202. The plurality of gear teeth 212 may engage a first of two or more torque links 58 that may be identical to those previously described, and the two or more torque links 58 may be disposed in the curved portion 142 of the shaft portion 140. As such, each of the plurality of gear teeth 212 at the distal end 204 of the torque member 202 may engage a corresponding one of the plurality of receiving notches 190a of the first torque link 58a such that a rotation of the torque member 202 causes a corresponding rotation of the first torque link 58a. The rotation of the first torque link 58a causes a corresponding rotation of the second torque line 58b (and any additional torque links 58) to rotate the end effector 48 relative to the distal end 44 of the shaft portion 40.

Advantageously, the torque member 202 efficiently transmits a torque applied to the proximal end 204 of the torque member 202 to the distal end 206 of the torque member 202 without rotational lag, allowing for precise rotational control and more immediate response when a user rotates the adjustment wheel 122.

Figure 5:
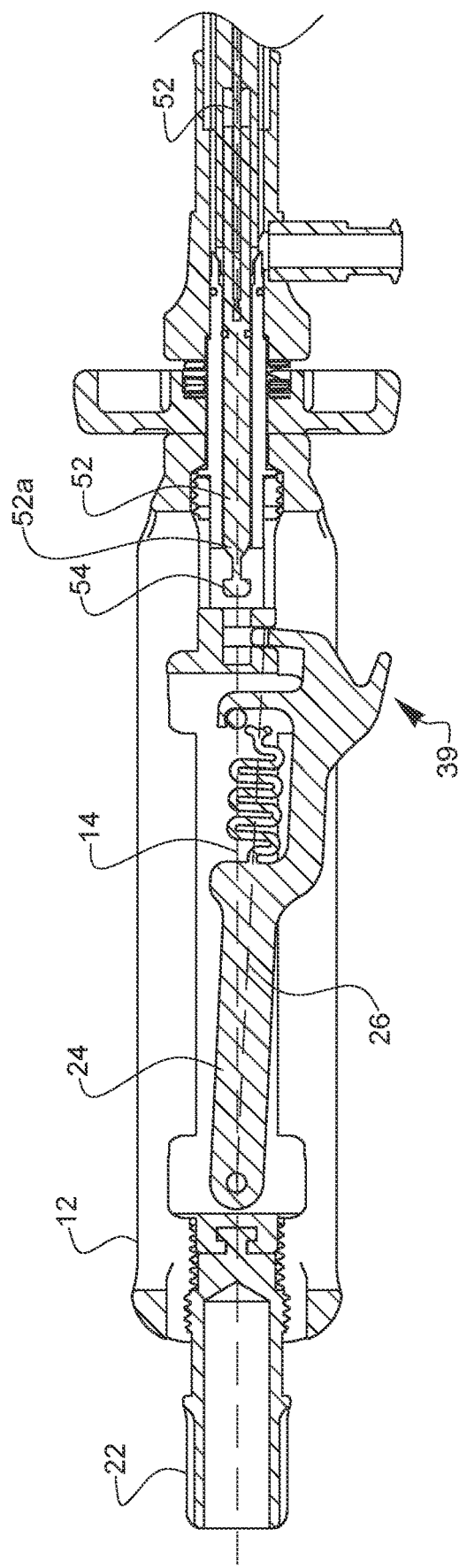
FIG. 5 is a cross-sectional view of the embodiment of the tissue manipulation device of FIG. 1 with the securing member in a disengaged position.

In some embodiments, the torque member 202 may not be a portion of the removable portion 57 that may be removed through the distal end 44 of the shaft portion 40 as a unit when the securing member 24 is pivoted from the engaged position 36 (illustrated in FIG. 4A) to the disengaged position 39 (illustrated in FIG. 5). However, in other embodiments, the torque member 202 may be a portion of the removable portion 57, and the proximal end 204 of the torque member 202 may be disposed adjacent to the proximal end 54 of the wire 52 or adjacent to a portion of the coupling portion 52a, In such an embodiment, a feature (not shown) coupled to or formed on the wire 52 (or coupling portion 52a) may prevent the proximal end 204 of the torque member 202 from displacing beyond the proximal end 54 of the wire 52 when the removable portion 57 is removed through the distal end 44 of the shaft portion 40.

For example, FIGS. 16 to 18D illustrate an embodiment of a removable portion 300 that may include an embodiment of a torque member 302. In this embodiment, the torque member 302 may extend along an axis 304 from a proximal end 306 to a distal end 308, and the axis 304 may be aligned with the portion of the shaft axis 47 that extends along the linear portion 140 of the shaft portion 40 (see FIG. 10A). The axis 304 may also be parallel to or aligned with (in an unbent or linear configuration) with the X-axis of the reference coordinate system of FIGS. 16 and 17A. The torque member 302 may be configured to transmit torque that is input at the proximal end 306 to the output end 308 when the torque member 302 is rotated about the axis 304. The torque member 302 may also be configured to allow for bending of the torque member 302 about an axis that is normal to the axis 304 such that the torque member 302 may bend only in a first bending plane, thereby allowing the torque member 302 to efficiently transmit torque without lag or loss from slop, while allowing one or more portions of the torque member 302 to selectively bend when the removable portion 300 to be passed through the curved portion 142 of the shaft portion 40 when inserting or removing the removable portion 300 for disassembly or reassembly.

Turning to FIG. 17A, the torque member 302 may include a base 310 that extends from the proximal end 306 to the distal end 308. The base 310 may have a constant cross-sectional shape along the length of the torque member 302. As illustrated in FIG. 17E, the cross-sectional shape of the base 310 (when viewed along the axis 304) may be defined by an upper edge 312 and a lower edge 314 that is parallel to and offset from the upper edge 312. Each of the upper edge 312 and a lower edge 314 may be parallel to the Y-axis of the reference coordinate system of FIGS. 16 and 17C. The cross-sectional shape of the base 310 may be further defined by a first lateral edge 316 and a second lateral edge 318. The first lateral edge 316 may extend along or substantially along the Z-axis of the reference coordinate system of FIGS. 16 and 17C from a first end of the upper edge 312 to a first end of the lower edge 314. The second lateral edge 318 may extend along or substantially along the Z-axis of the reference coordinate system of FIGS. 16 and 17C from a second end of the upper edge 312 to a second end of the lower edge 314. Each of the first lateral edge 316 and the second lateral edge 318 may be curved to partially curved to form a segment of a circle, for example.

Figure 16:
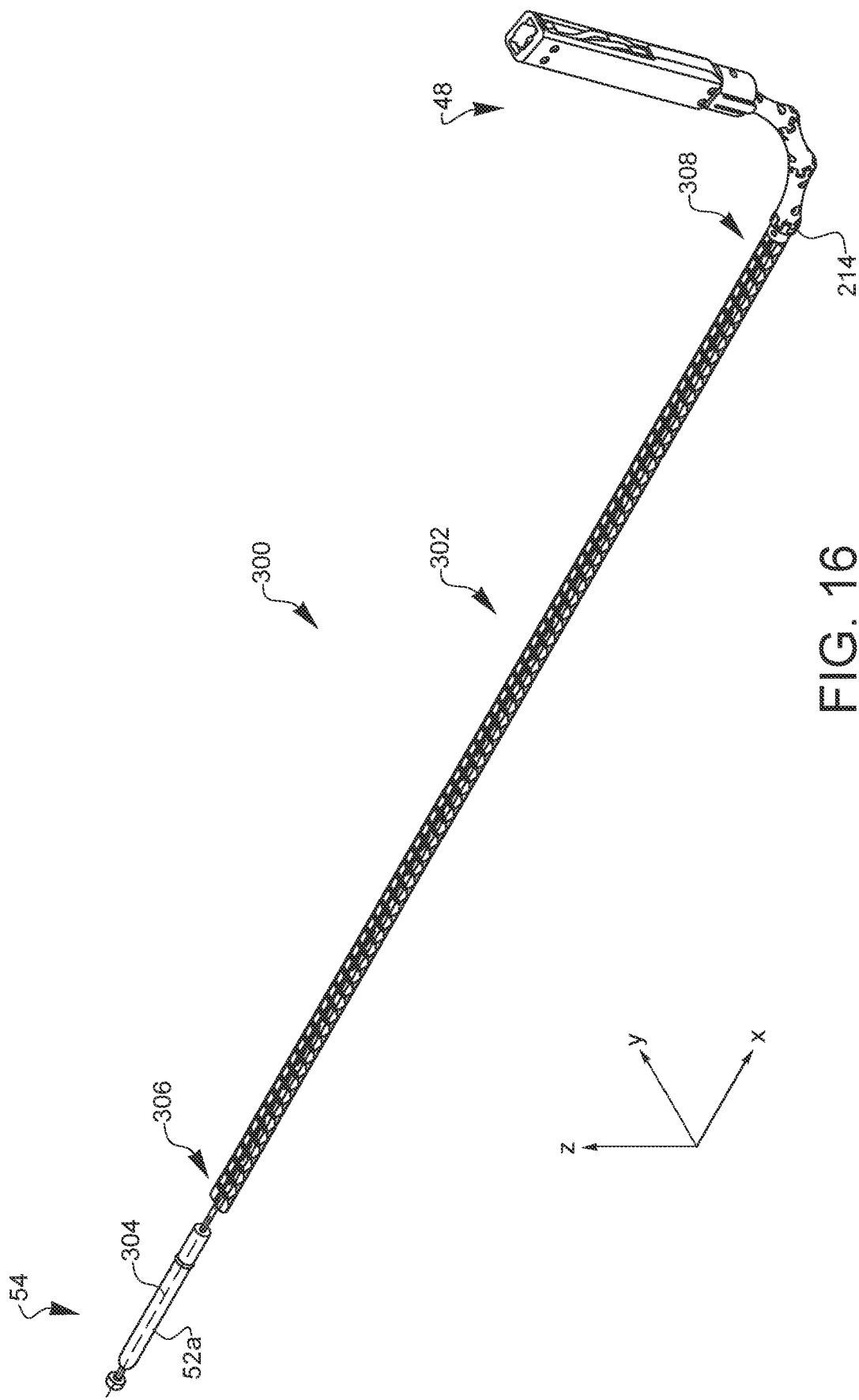
FIG. 16 is a perspective view of an embodiment of the removable portion of an embodiment of the tissue manipulation device.

A plurality of projections 320 may extend from the base 310, and each of the plurality of projections 320 may be spaced along the X-axis of the reference coordinate system of FIGS. 16 and 17C from an adjacent other of the plurality of projections 320. The plurality of projections 320 may extend along the entire length of the base 310 from the proximal end 306 to the distal end 308 of the torque member 302. In other embodiments, the plurality of projections 320 may extend along one or more portions of the length of the base 310. When viewed in cross-section (along the axis 304), as illustrated in FIG. 17C, each of the plurality of projections 320 may be include a first projection portion 322a and a second projection portion 322b, and the first projection portion 322a and the second projection portion 322b may be symmetrically formed about a plane 325, which is parallel to the X-Z plane of the reference coordinate system of FIGS. 16 and 17C, and the plane 325 may extend along the axis 304. The first projection portion 322a may be defined by an upper projection edge 326a and a lower projection edge 328a. The lower projection edge 238a may extend along or generally along the Y-axis of the reference coordinate system of FIGS. 16 and 17C, and the upper projection edge 326a may be obliquely disposed (or downwardly sloped) towards the lower projection edge 328a as the upper projection edge 326a extends away from the plane 325. A lateral edge 330a may extend between a first end of the upper projection edge 326a and a first end of the lower projection edge 328a, and the lateral edge 330a may be at least partially curved or rounded. As such, the upper projection edge 326a, the lower projection edge 328a, and the lateral edge 330a may cooperate to generally form shape of a wedge. A second lateral edge 332a may extend from a second end of the lower projection edge 328a to a first portion of the upper edge 312 of the base 310, and the second lateral edge 332a may be least partially curved or rounded.

The second projection portion 322b may be a mirror image of the first projection portion 322a and may be symmetrical to the first projection portion 322a about the plane 325. In particular, the second projection portion 322b may be defined by an upper projection edge 326b and a lower projection edge 328b. The lower projection edge 238b may extend along or generally along the Y-axis of the reference coordinate system of FIGS. 16 and 17C, and the upper projection edge 326b may be obliquely disposed (or downwardly sloped) towards the lower projection edge 328b as the upper projection edge 326b extends away from the plane 325. A lateral edge 330b may extend between a first end of the upper projection edge 326b and a first end of the lower projection edge 328b, and the lateral edge 330b may be curved or rounded. As such, the upper projection edge 326b, the lower projection edge 328b, and the lateral edge 330b may cooperate to generally form shape of a wedge. A second lateral edge 332b may extend from a second end of the lower projection edge 328b to a second portion of the upper edge 312 of the base 310, and the second lateral edge 332a may be least partially curved or rounded.

Each of the plurality of projections 320 may also include a wire bore 334 that extends from a proximal end of each of the plurality of projections 320 to a distal end of each of the plurality of projections 320. Each of the wire bores 334 in each of the plurality of projections 320 may be aligned or generally aligned with the other plurality of projections 320 over the length of the axis 304 such that, in operation, a corresponding portion of the wire 52 may be disposed through, and be longitudinally displaceable within, the wire bore 334 of each of the plurality of projections 320. The wire bore 334 may have any suitable shape to receive the corresponding portion of the wire 52. For example, the wire bore 334 may be a substantially U-shaped notch 336 formed between the first projection portion 322a and the second projection portion 322b, and the notch may extend through and along the plane 325. The notch may have a first lateral portion 338a that extends downwardly from a second end of the upper projection edge 326a of the first projection portion 322a and a second lateral portion 338b that extends downwardly from a second end of the upper projection edge 326b of the second projection portion 322b. A notch end edge 340 may extend (e.g., extend parallel to or generally parallel to the Y-axis of the reference coordinate system of FIGS. 16 and 17C) between an end of the first lateral portion 338a and an end of the second lateral portion 338b.

With reference to FIG. 17A, each of the plurality of projections 320 may be spaced along the X-axis of the reference coordinate system of FIGS. 16 and 17C from an adjacent other of the plurality of projections 320. For example, a first 320a of the plurality or projections 320 may have a distal lateral edge 342a that may be disposed a first distance D1 along the X-axis from a proximal lateral edge 344b of a second 320b of the plurality or projections 320. The second 320a of the plurality or projections 320 may have a distal lateral edge 342b that may be disposed a second distance D2 along the X-axis from a proximal lateral edge 344c of a third 320c of the plurality or projections 320. In some embodiments, the first distance D1 may be equal to the second distance D2. In some embodiments, the distance along the X-axis between a distal lateral edge 342x of any of the plurality of projections 320 from a proximal lateral edge 344x of an adjacent one of the plurality of projections 320 may be the first distance D1.

As illustrated in FIG. 17A, when viewed along the Y-axis of the reference coordinate system, a first neck edge 346 and a second neck edge 348 extends obliquely towards the base 310 to form a narrowed neck portion 350 that upwardly extends from the base 310. The spacing between the first and second adjacent plurality of projections 320, as well as the combination of cross-sectional shapes of each of the plurality of projections 320, allow the torque member 302 to bend along an axis that is parallel to the Y-axis of the reference coordinate system of FIGS. 16 and 17A, that this axis may be normal to the plane 325. Thus, any portion of the torque member 302 may bend clockwise or counterclockwise about the axis when viewed along the Y-axis, as shown in FIG. 17A. Thus, rotation is allowed in a single bending plane (plane 325), but no along any other planes or along any axis that is not parallel to the Y-axis of the reference coordinate system of FIGS. 16 and 17A. This ensure sufficient rigidity of the torque member 302 when the torque member 302 is rotated about the X-axis of the reference coordinate system of FIGS. 16 and 17A while allowing the torque member 302 to bend within a single plane to allow for insertion or extraction of the removable portion 300 through the curved portion 142 of the shaft portion 40.

As illustrated in FIGS. 18A to 18D, the torque member 302 may also include one or more alignment features 352 that ensures that the removable portion 300 is oriented correctly when inserted into the distal end 44 of the shaft portion 40 during the assembly (or reassembly) of the tissue manipulating device 10. The one or more alignment features 352 may include a protrusion 356 formed at or adjacent to the distal end 354 of the linear portion 140 of the shaft portion 40 or at or adjacent to the proximal end of the curved portion 142 of the shaft portion 40. The protrusion 356 may be formed as a depression (e.g., a dome-shaped depression) in the shaft portion 40 and the depression may extend into the shaft interior portion 146. In some embodiments, the depression may be a dome-shaped depression that may be symmetrically formed or disposed about a plane that extends through the shaft axis 47 and is parallel to the X-Z of the reference coordinate system of FIGS. 1 and 18D, and the depression may be formed on an upper surface of the shaft portion 40, wherein the direction "upper" corresponds to the direction along the Z-axis in which the curved portion 142 of the shaft portion 40 extends.

The alignment feature 352, such as the depression, may be positioned to not contact a portion of the upper projection edges 326a, 326b of the first projection portion 322a or the second projection portion 322b of the torque member 302 when the removable portion 300 is positioned correctly for insertion. However, when the removable portion 300 is positioned incorrectly upon insertion into the shaft portion 40, the alignment feature 352 may contact a portion of the sloped upper projection edges 326a, 326b of the first projection portion 322a or the second projection portion 322b to rotate the torque member 302, and the entire removable portion 300, into correct alignment to allow for the curving of the torque member 302 upon insertion into the shaft portion 40. FIG. 18C illustrates various orientations of the torque member 302 relative to the alignment feature 352 within the shaft portion 40.

Figure 19A:
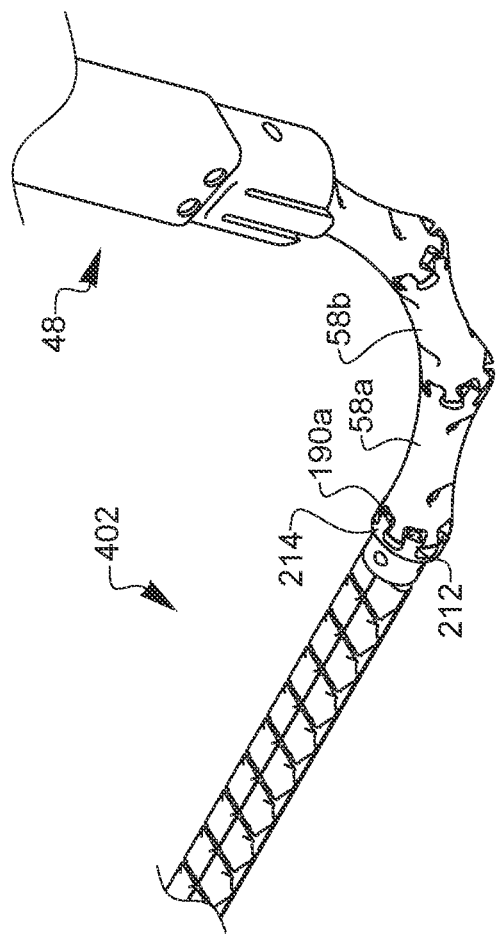
FIG. 19A is a partial perspective view of an embodiment of a torque member of a removable portion of an embodiment of the tissue manipulation with the shaft portion removed for clarity.
Figure 19B:
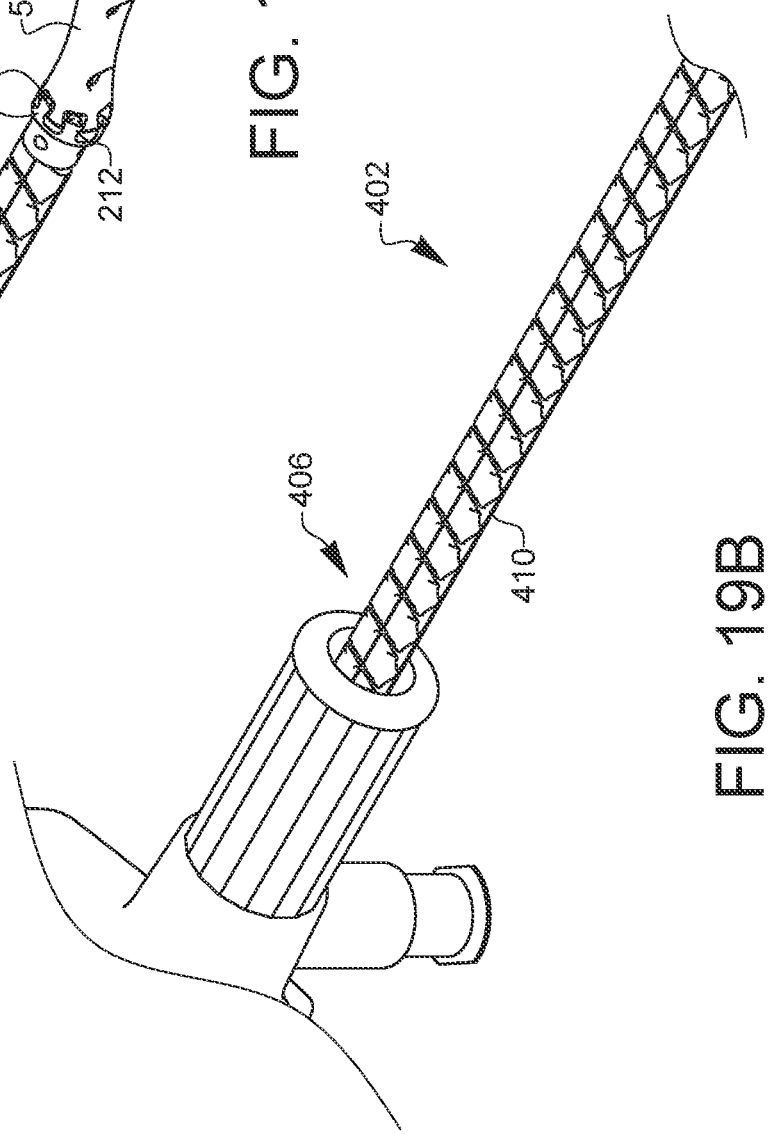
FIG. 19B is a further partial perspective view of the embodiment of the torque member of the removable portion of FIG. 19A with the shaft portion removed for clarity.
Figure 19E:
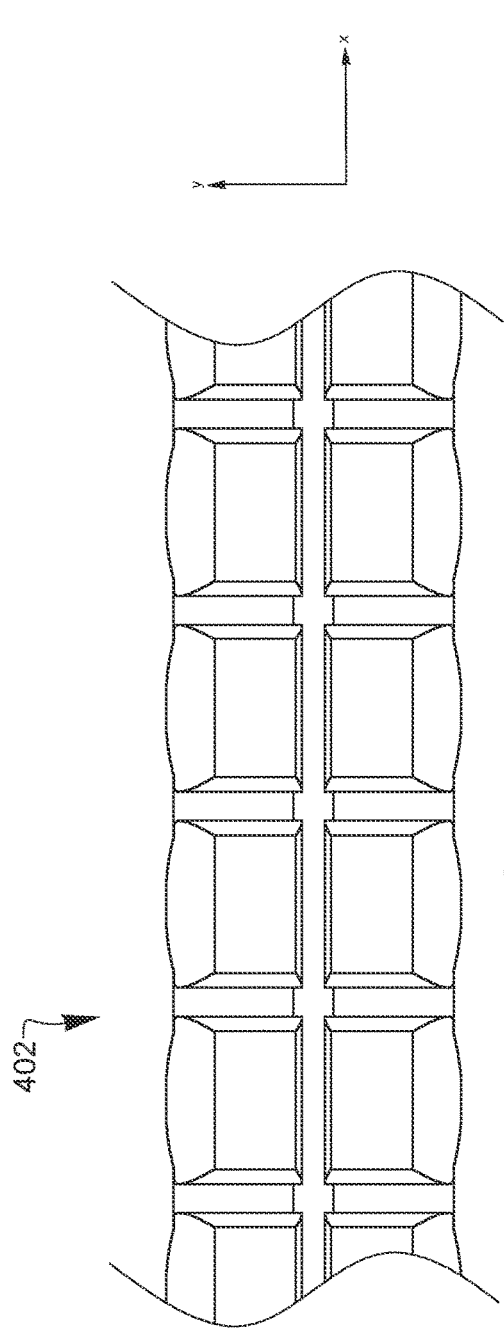
FIG. 19E is top view of a portion of the torque member of the removable portion of the embodiment of the tissue manipulation device of FIG. 19A.
Figure 19F:
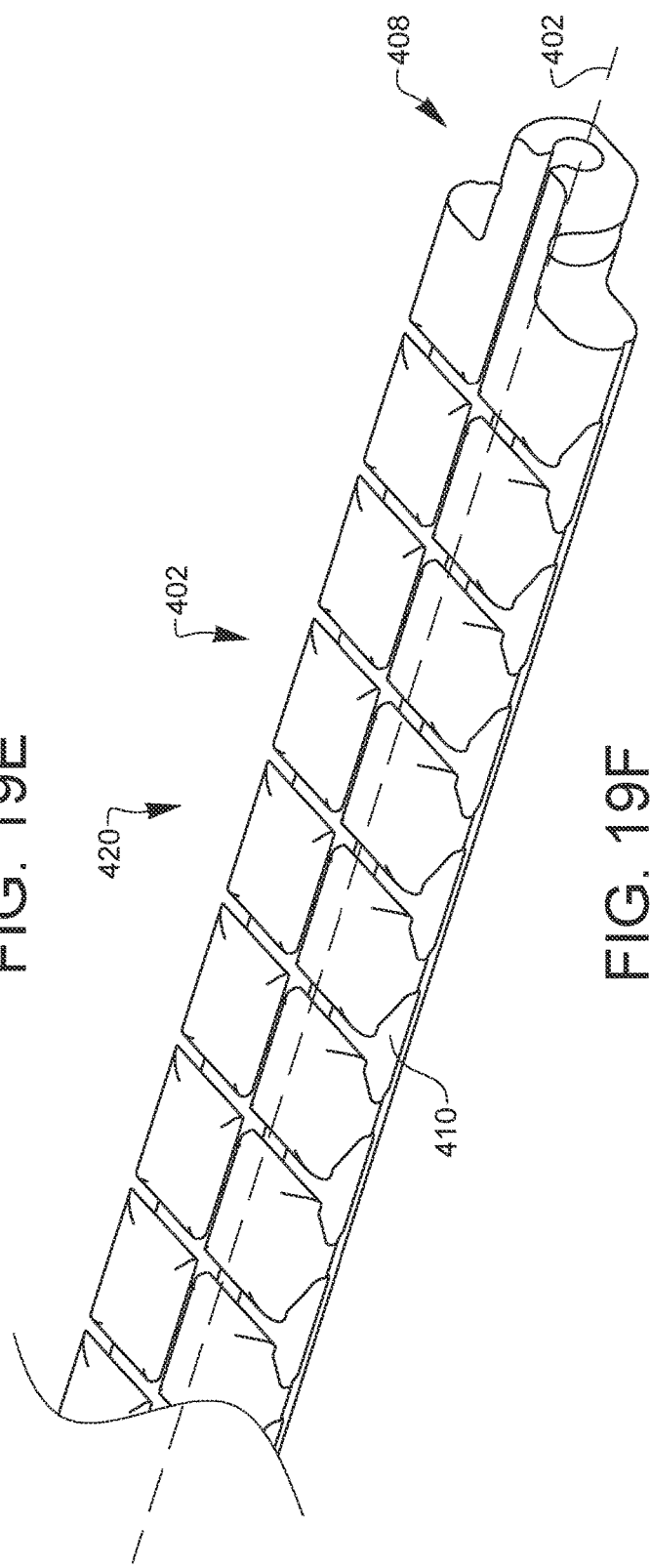
FIGS. 19F to 19H are various partial perspective views of the torque member of the removable portion of the embodiment of the tissue manipulation device of FIG. 19A.
Figure 19G:
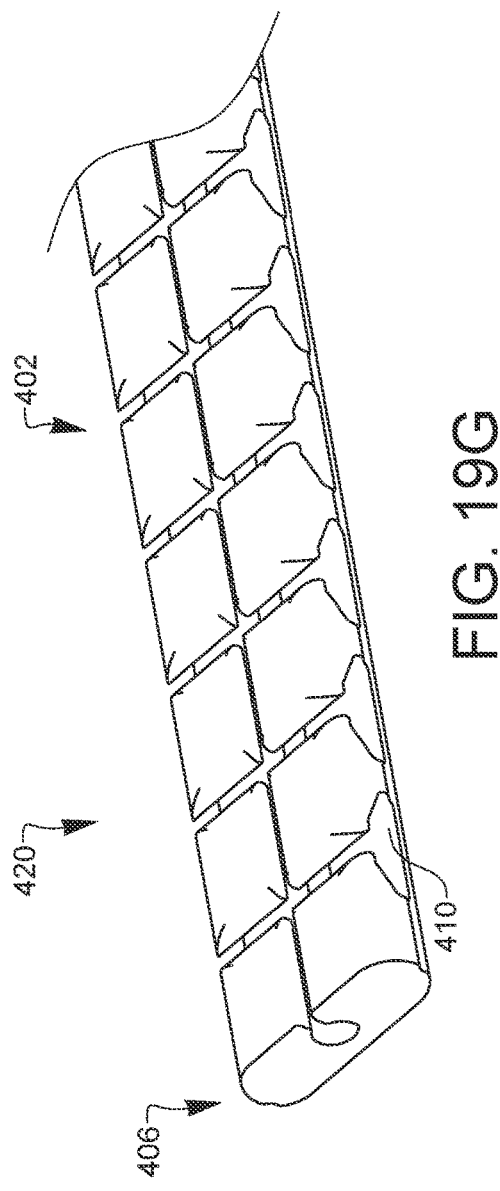
Figure 19H:
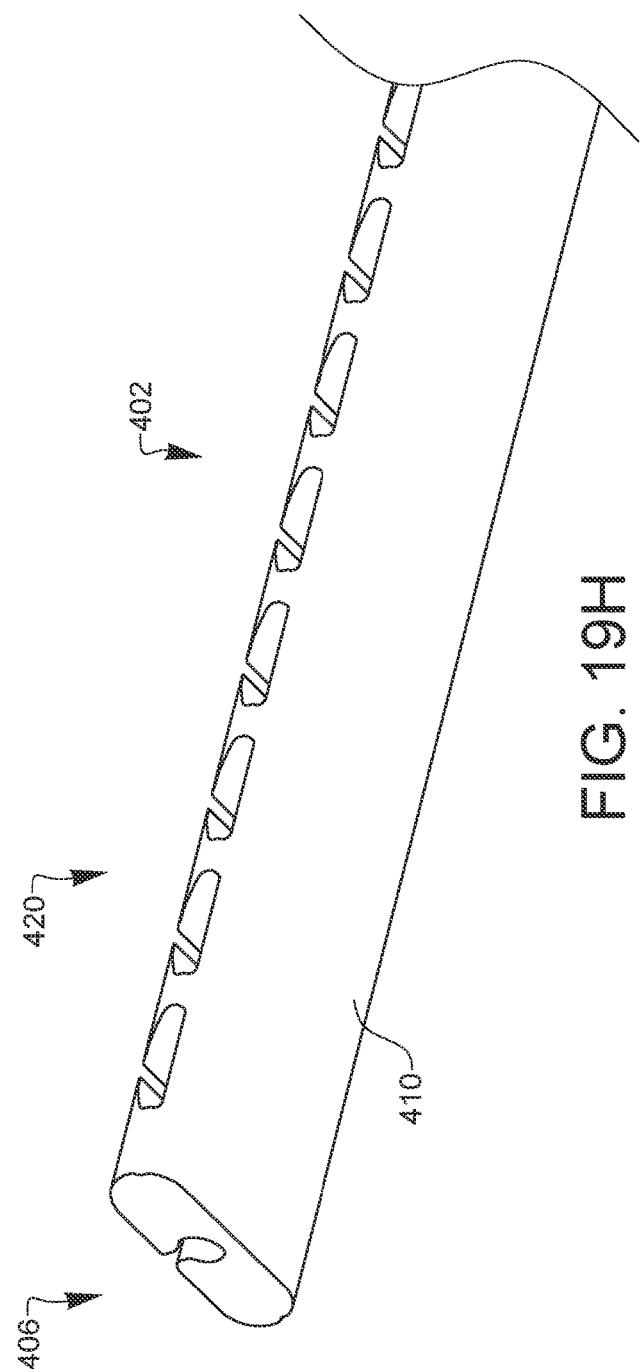
Figure 19I:
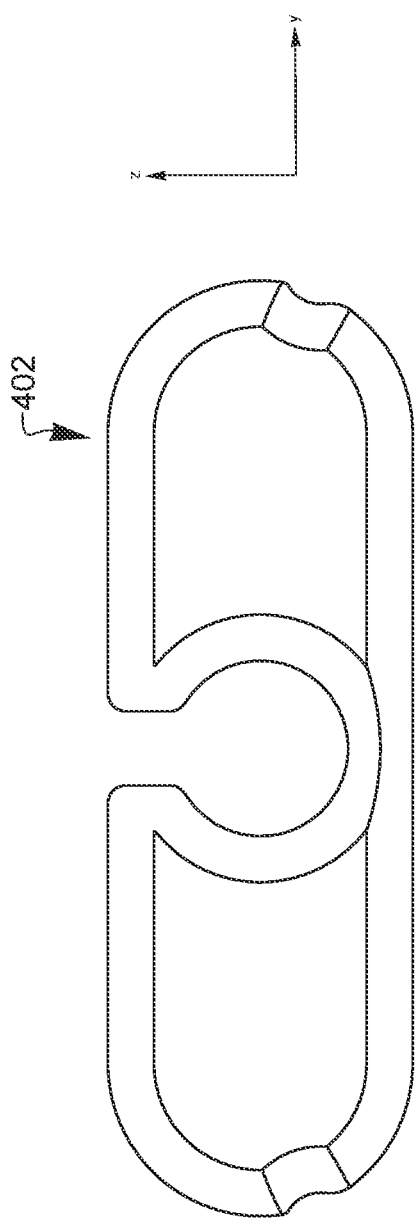
FIG. 19I is a front view of the torque member of the removable portion of the embodiment of the tissue manipulation device of FIG. 19A.
Figure 19J:
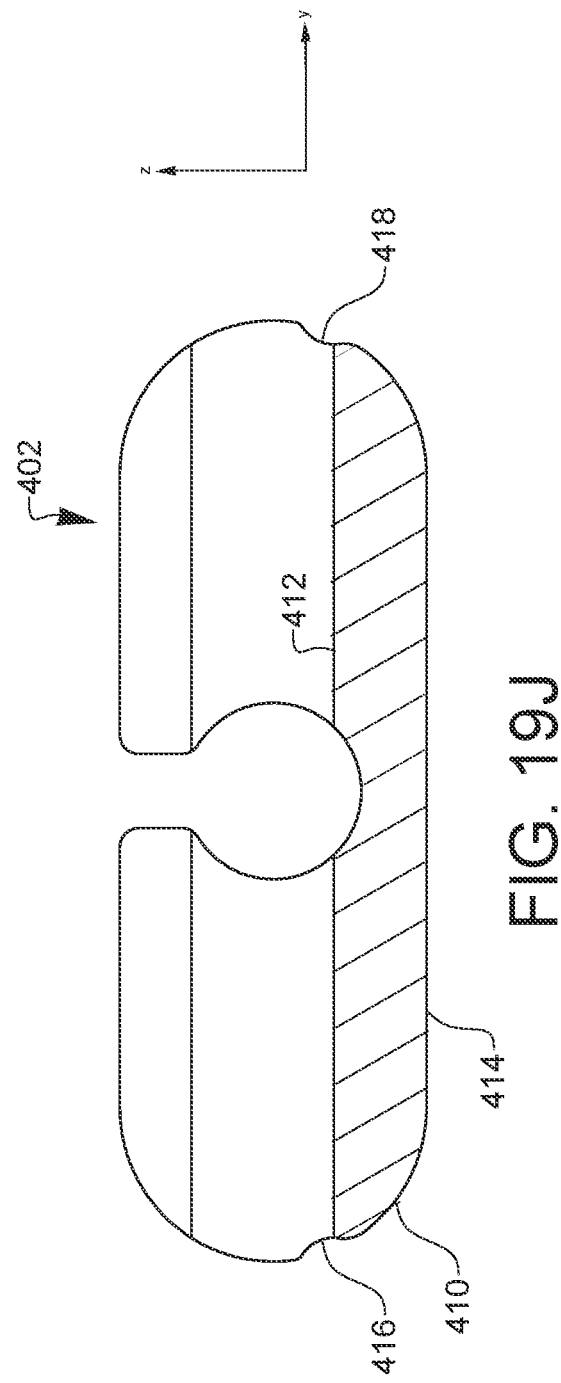
FIG. 19J is a cross-sectional view of the embodiment of the torque member taken along section line 19J-19J in FIG. 19D.
Figure 19K:
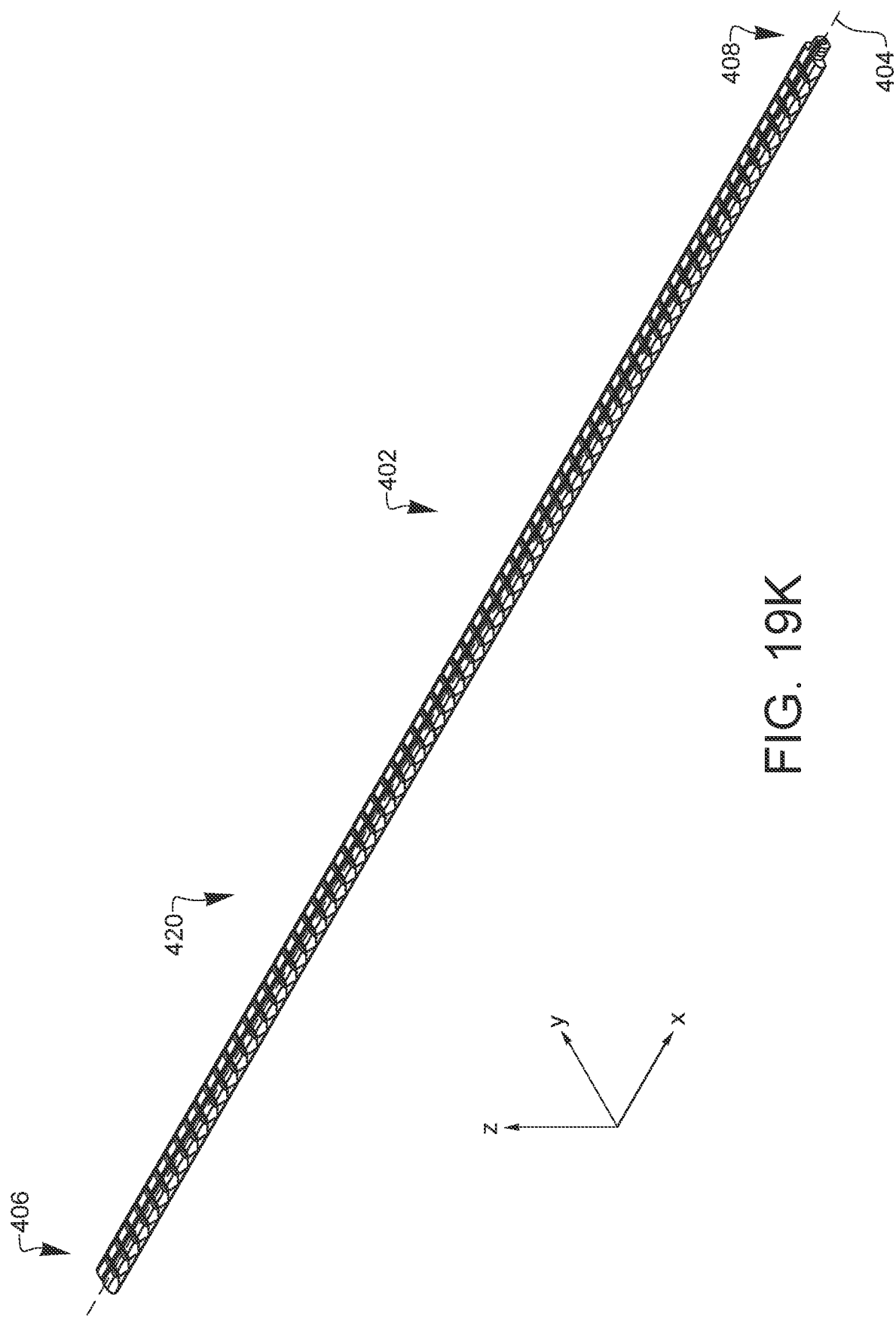
FIG. 19K is a perspective view of the embodiment of the torque member of the removable portion of FIG. 19A.

FIGS. 19A to 19K illustrate a further embodiment of a removable portion 400 that may include an embodiment of a torque member 402 that may be similar to, but have a slightly different cross-sectional shape from, the torque member 302 illustrated in FIGS. 16 to 18D. As illustrated in FIG. 19K, the torque member 402 may extends along an axis 404 from a proximal end 406 to a distal end 408, and the torque member 402 may include a base 410 that extends from the proximal end 406 to the distal end 408. The base 410 may have a constant cross-sectional shape along the length of the torque member 402. As illustrated in FIG. 19J, the cross-sectional shape of the base 410 (when viewed along the axis 404) may be defined by an upper edge 412 and a lower edge 314 that is parallel to and offset from the upper edge 412. Each of the upper edge 412 and a lower edge 414 may be parallel to the Y-axis of the reference coordinate system of FIG. 19J. The cross-sectional shape of the base 410 may be further defined by a first lateral edge 416 and a second lateral edge 418. The first lateral edge 416 may extend along or substantially along the Z-axis of the reference coordinate system of FIG. 19J from a first end of the upper edge 412 to a first end of the lower edge 414. The second lateral edge 418 may extend along or substantially along the Z-axis of the reference coordinate system of FIG. 19J from a second end of the upper edge 412 to a second end of the lower edge 414. Each of the first lateral edge 416 and the second lateral edge 418 may be curved, contoured, or partially curved.

A plurality of projections 420 may extend from the base 410, and each of the plurality of projections 420 may be spaced along the X-axis of the reference coordinate system of FIG. 19D from an adjacent other of the plurality of projections 420. The plurality of projections 420 may extend along the entire length of the base 410 or may extend along one or more portions of the length of the base 410. When viewed in cross-section (along the axis 404), as illustrated in FIG. 19C, each of the plurality of projections 420 may be include a first projection portion 422a and a second projection portion 422b, and the first projection portion 422a and the second projection portion 422b may be symmetrically formed about a plane 425, which is parallel to the X-Z plane of the reference coordinate system of FIGS. 19C and 19D, and the plane 425 may extend along the axis 404. The first projection portion 422a may be defined by an upper projection edge 426a which may extend along or generally along the Y-axis of the reference coordinate system of FIG. 19C, and a lateral edge 430a may extend between a first end of the upper projection edge 326a and a first end of the base 410 (e.g., a first end of the upper edge 412 of the base 410), and the lateral edge 430a may be at least partially curved or rounded. The second projection portion 422b may be a mirror image of the first projection portion 422a and may be symmetrical to the first projection portion 422a about the plane 425. In particular, the second projection portion 422b may be defined by an upper projection edge 426b which may extend along or generally along the Y-axis of the reference coordinate system of FIG. 19C, and a lateral edge 430b may extend between a first end of the upper projection edge 426b and a second end of the base 410 (e.g., a second end of the upper edge 412 of the base 410), and the lateral edge 430b may be at least partially curved or rounded.

Each of the plurality of projections 420 may also include a wire bore 434 that from a proximal end of each of the plurality of projections 420 to a distal end of each of the plurality of projections 420. Each of the wire bores 434 in each of the plurality of projections 420 may be aligned or generally aligned with the other plurality of projections 420 over the length of the axis 404 such that, in operation, a corresponding portion of the wire 52 may be disposed through, and be longitudinally displaceable within, the wire bore 434 of each of the plurality of projections 420. The wire bore 434 may have any suitable shape to receive the corresponding portion of the wire 52. For example, the wire bore 434 may be a substantially U-shaped notch 436 formed between the first projection portion 422a and the second projection portion 422b, and the notch 436 may extend through and along the plane 425. The notch 436 may have a first lateral portion 438a that extends downwardly from a second end of the upper projection edge 426a of the first projection portion 422a and a second lateral portion 438b that extends downwardly from a second end of the upper projection edge 426b of the second projection portion 422b. A notch bottom edge 440 may extend between an end of the first lateral portion 438a and an end of the second lateral portion 438b, and the notch bottom edge 440 may have the shape of a segment of a circle.

With reference to FIG. 19D, each of the plurality of projections 420 may be spaced along the X-axis of the reference coordinate system of FIGS. 19D and 19K from an adjacent other of the plurality of projections 420. For example, a first 420a of the plurality or projections 420 may have a distal lateral edge 442a that may be disposed a first distance D1 along the X-axis from a proximal lateral edge 444b of a second 420b of the plurality or projections 420. The second 420a of the plurality or projections 420 may have a distal lateral edge 442b that may be disposed a second distance D2 along the X-axis from a proximal lateral edge 444c of a third 420c of the plurality or projections 420. In some embodiments, the first distance D1 may be equal to the second distance D2. In some embodiments, the distance along the X-axis between a distal lateral edge 442x of any of the plurality of projections 420 from a proximal lateral edge 444x of an adjacent one of the plurality or projections 420 may be the first distance D1.

As illustrated in FIG. 19D, when viewed along the Y-axis of the reference coordinate system, a first neck edge 446 and a second neck edge 448 extends obliquely towards the base 410 to form a narrowed neck portion 450 that extends upward from the base 410. The spacing between the first and second adjacent plurality of projections 420, as well as the combination of cross-sectional shapes of each of the plurality of projections 420, allow the torque member 402 to bend along an axis that is parallel to the Y-axis of the reference coordinate system of FIGS. 19C and 19D, that this axis may be normal to the plane 425. Thus, any portion of the torque member 402 may bend clockwise or counterclockwise about the axis when viewed along the Y-axis, as shown in FIG. 19D. Thus, rotation is allowed in a single bending plane (plane 425), but not along any other planes or along any axis that is not parallel to the Y-axis of the reference coordinate system of FIG. 19D. This ensures sufficient rigidity of the torque member 402 when the torque member 402 is rotated about the X-axis of the reference coordinate system of FIGS. 19D and 19K while allowing the torque member 402 to bend within a single plane to allow for insertion or extraction of the removable portion 400 through the curved portion 142 of the shaft portion 40.

FIGS. 20A to 20F illustrate a further embodiment of a removable portion 500 that may include an embodiment of a torque member 502 that may be similar to, but have a different cross-sectional shape from, the torque member 302 illustrated in FIGS. 16 to 18D and the torque member 402 illustrated in FIGS. 19A to 19K. As illustrated in FIG. 19A, the torque member 502 may extends along an axis 504 from a proximal end 506 to a distal end 508, and the torque member 502 may include a base 510 that extends from the proximal end 506 to the distal end 508, and the base 510 may be similar to the base 410 of base 310 previously described.

Figure 20A:
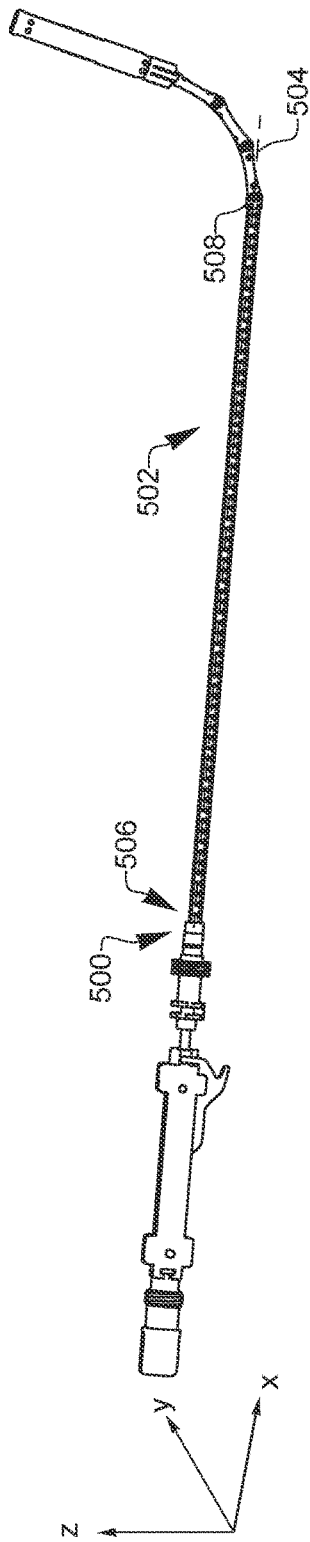
FIG. 20A is a perspective view of an embodiment of the tissue manipulation device with the shaft portion removed for clarity.
Figure 20B:
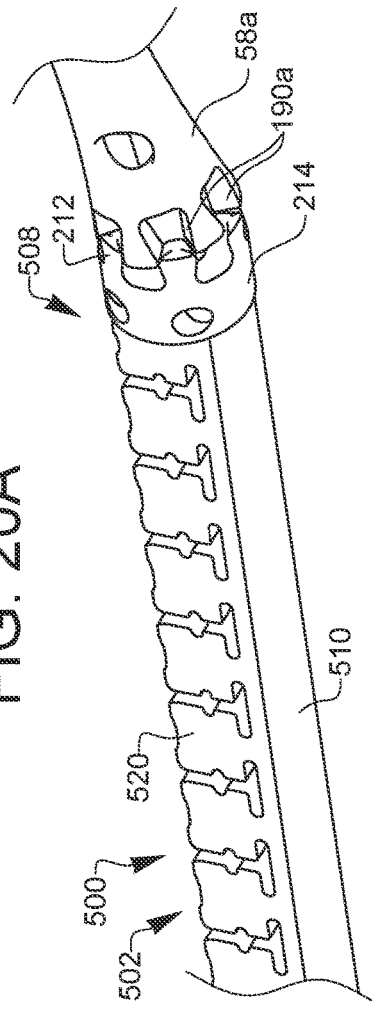
FIG. 20B is a perspective view of a portion of the embodiment of the tissue manipulation device of FIG. 20A with the shaft portion removed for clarity.

A plurality of projections 520 may extend from the base 510, and each of the plurality of projections 520 may be spaced along the X-axis of the reference coordinate system of FIG. 20A from an adjacent other of the plurality of projections 420, in a manner similar or identical to the plurality of projections 420 or the plurality of projections 320 previously described. Each of the plurality of projections may have a rectangular of square (or substantially rectangular or square) cross-sectional shape, as illustrated in FIG. 20F. Each of the plurality of projections 520 may also include a wire bore 534 that extends from a proximal end of each of the plurality of projections 520 to a distal end of each of the plurality of projections 520. Each of the wire bores 534 in each of the plurality of projections 520 may be aligned or generally aligned with the other plurality of projections 520 over the length of the axis 504 such that, in operation, a corresponding portion of the wire 52 may be disposed through, and be longitudinally displaceable within, the wire bore 534 of each of the plurality of projections 520. The wire bore 534 may have any suitable shape to receive the corresponding portion of the wire 52. For example, the wire bore 534 may be cylindrical and may have an axis that extends parallel to the X-axis of the reference coordinate system of FIG. 20C. In cross-section, the wire bore 534 may have a circular edge 540 that may be symmetrically disposed about a plane 525 that is parallel to the X-Z plane of the reference coordinate system of FIG. 20A, and the plane 525 may extend along the axis 504.

Figure 20C:
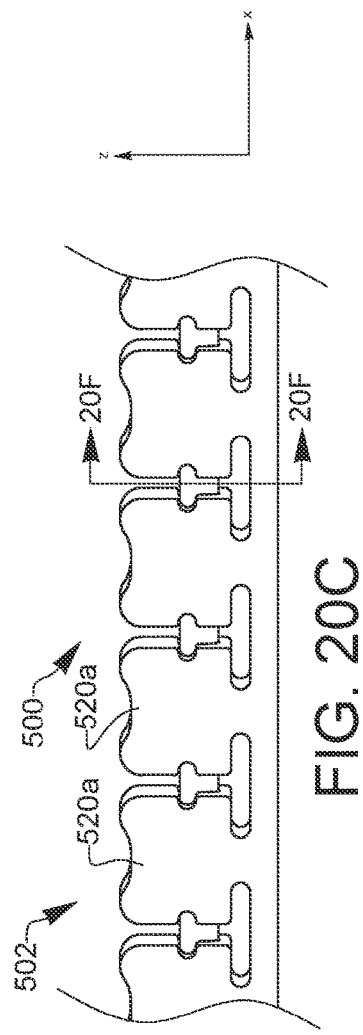
FIG. 20C is side view of the torque member of the removable portion of the embodiment of the tissue manipulation device of FIG. 20A.

With reference to FIG. 20C, each of the plurality of projections 520 may be spaced along the X-axis of the reference coordinate system of FIG. 20C from an adjacent other of the plurality of projections 520 in a manner identical to that of the plurality of projections 420 or the plurality of projections 320 previously described. The spacing between the first and second adjacent plurality of projections 520, as well as the combination of cross-sectional shapes of each of the plurality of projections 520, allow the torque member 502 to bend along an axis that is parallel to the Y-axis of the reference coordinate system of FIG. 20A, that this axis may be normal to the plane 525. Thus, any portion of the torque member 502 may bend clockwise or counterclockwise about the axis when viewed along the Y-axis, as shown in FIG. 20C. Thus, rotation is allowed in a single bending plane (plane 525), but not along any other planes or along any axis that is not parallel to the Y-axis of the reference coordinate system of FIG. 20A. As previously explained, this ensures sufficient rigidity of the torque member 502 when the torque member 502 is rotated about the X-axis of the reference coordinate system of FIG. 20A while allowing the torque member 502 to bend within a single plane to allow for insertion or extraction of the removable portion 500 through the curved portion 142 of the shaft portion 40.

The torque member 202 may be comprised of any suitable material or combination of materials, such as plastic or stainless steel.

Referring again to FIG. 1, the tissue manipulation device 10 may include a port 214 that extends from a portion of the housing portion 12, such as a portion of the distal support portion 112 of the wheel housing portion 108. As illustrated in FIG. 3, the port 214 may be cylindrical and may extend from an inner end 216 to an outer end 218 along an axis that may be transverse to the longitudinal axis 14. The inner end 216 may be in communication with a chamber 219 within the distal support portion 112 and adjacent to the proximal end 42 of the shaft portion 40. One or more seals may be disposed on the wheel hub 170 to prevent fluid in the chamber 219 from moving proximally. The shaft portion 40 may include a plurality of apertures 220 that may be at least partially disposed on the curved portion 142 of the shaft portion 40. Each of the plurality of apertures 220 extends from the exterior surface 145 of the shaft portion 40 to the shaft interior portion 146. One or more seals may be disposed distal to the plurality of apertures 220 to prevent fluid from moving distal to the one or more seals. As such, when a fluid is introduced into the outer end 218 of the port 214, the fluid travels through the port 214 and into the chamber 219, where the fluid enters the shaft interior portion 146 and travels distally towards the plurality of apertures 220, where the fluid exits each of the plurality of apertures 220. One having ordinary skill in the art would recognize that the fluid would flow in any gaps or passages associated with components disposed within the shaft interior portion 146. For example, one having ordinary skill in the art would recognize that the fluid would flow through the link bores 286 of the torque links 58 or through gaps between the torque links 58 and portions of the one or more interior surfaces 147 defining the shaft interior portion 146. The outer end 218 of the port 214 may be configured to connect to a source of fluid, and may have a luer fitting, for example. The fluid may be a liquid or gas that may be delivered to a treatment area of a patient that is at or adjacent to at least one of the plurality of apertures 220. In operation, fluid may also be removed from the treatment area by entering any of the plurality of apertures 220 and exiting the outer end 218 of the port 214.

The tissue manipulation device 10 may be fabricated using any suitable material or combination of materials, such as materials that allow for the cleaning and sterilization of all or parts of the tissue manipulation device 10 (e.g., a plastic material or stainless steel). For example, all or portions of the handle portion 12, the shaft portion 12, and the end effector 48 may all be composed or made from stainless steel or plastic.

In operation, the tissue manipulation device 10 may be used in a prostatectomy procedure. In particular, the tissue manipulation device 10 may be inserted transurethral by an operator, e.g., surgeon, into the penis of a patient, and the curved portion 142 of the shaft portion 140 allows the shaft portion 140 to travel along the patient's urethra and past the bony diaphragm structure of the pelvis until the distal end 152 of the housing of the end effector 48 is located in the patient's prostate. Once in the prostate, the adjustment member 22 may be rotated by the surgeon to drive the tissue engaging members 20 to extend into the prostate. Barbs 38 and 46 on the tissue engaging members facilitate gripping of the prostate. Although the tissue engaging members 20 are shown fully extended, in FIG. 8, they may be extended to any desired degree by the surgeon until full extension. The prostate's position can then be manipulated as needed to facilitate prostatectomy. The positioning of the prostate is provided under control of the surgeon, such as, raised or lowered by adjusting the tilt angle of the shaft portion 140 with respect to the patient's body, pulled or pushed by changing the extent of the shaft portion 140 passing through the urethra (i.e., slightly pushing or pulling the handle portion 12), and, advantageously, bi-directionally rotated using the adjustment wheel 24. In this manner, the surgeon can position the prostate to expose and apply tension to the tissue at the anterior side of the prostate, and thereby locate the area or zone of dissection and proceed to mobilize (or cut the surrounding tissue of) the prostate at its anterior side. The prostate's position may then be further manipulated with the tissue manipulation device 10 to facilitate exposing and placing under tension the area or zone of dissection and proceed to mobilize the tissue (or cut the surrounding tissue) along the posterior side and both lateral sides of the prostate. Once the prostate has been dissected, turning adjustment member 22 may retract the tissue engaging members 20. The prostate can then be removed from the patient and the urethra sutured to the bladder.

The tissue manipulation device 10 thus provides a surgical instrument, which is useful in either open surgery or a laparoscopic prostatectomy, but may also be used in other surgical procedures to manipulate tissue structures other than the prostate via a natural or surgical opening or channel in the body of a patient. The control of the prostate's position enabled by the multiple degrees of rotational freedom of the tissue manipulation device 10 allows for precise dissection thereby minimizing the risk of damage to the neurovascular bundles and other tissue about the prostate.

In some embodiments, the tissue manipulation device 10 may be configured for use in a robotic surgical procedure. For example, a robot (not shown) with a dynamic member, such as an arm, my interface with an embodiment of the tissue manipulation device 10 to position the tissue manipulation device 10 during the procedure. The robot, via a first robotic interface 236 (an embodiment of which is illustrated in FIG. 14A) be directly or indirectly coupled to the tissue manipulation device 10 to rotate the adjustment wheel 122 (or an equivalent mechanism or gear) to rotate the end effector 48 about the end effector axis 153 relative to the distal end 44 of the shaft portion 40 to precisely position the end effector 48 during a procedure. The first robotic interface 236 may be any mechanism, assembly, or device that may interact or interface with the tissue manipulation device 10 to cause the adjustment wheel 122 (or any portion of the rotational assembly coupled to the adjustment wheel 122) to rotate. For example, in the embodiment of FIG. 14A, the first robotic interface 236 may be a gear 238 that interfaces with the adjustment wheel 122 (or an equivalent gear that acts as the adjustment wheel 122) to rotate the adjustment wheel 122. Instead of a single gear 238, the first robotic interface 236 may include any number or combination of gears to turn the adjustment wheel 122 to a desired position. In other embodiments, such as that of FIG. 14C, the first robotic interface 236 may be a drive pulley 240 with a belt 242 that is coupled the adjustment wheel 122 to rotate the adjustment wheel 122. In the embodiment of FIG. 14B, the drive pulley 240 and belt 242 may be coupled to a pulley equivalent to the adjustment wheel 122 to rotate the adjustment wheel 122.

Figure 15B:
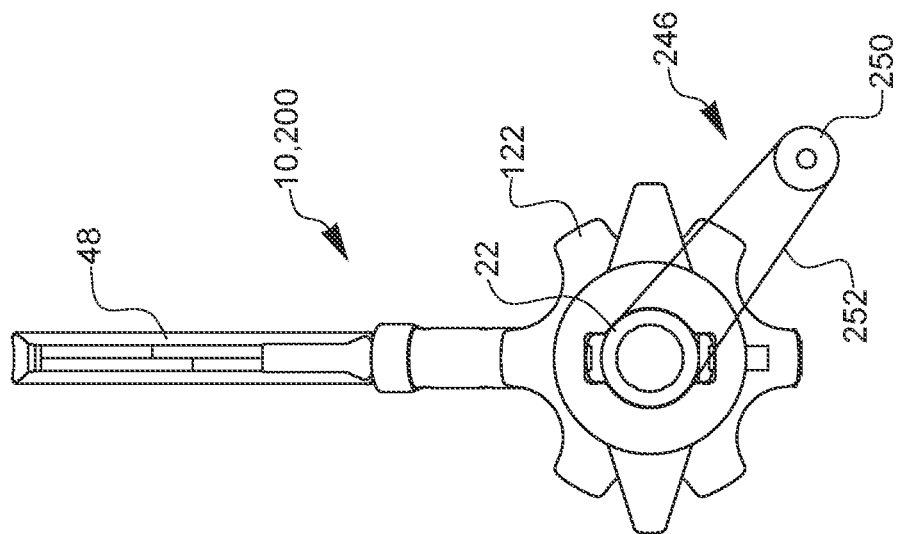
FIG. 15B is a rear view of an embodiment of the tissue manipulation device coupled to an embodiment of a second robotic interface.
Figure 15A:
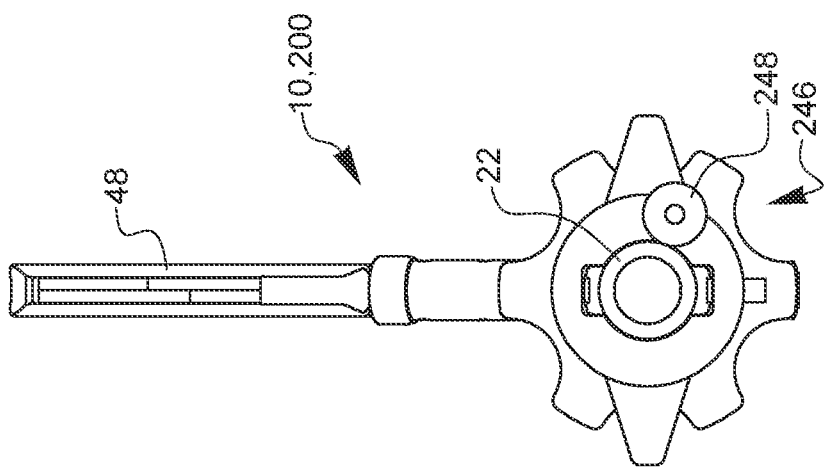
FIG. 15A is a rear view of an embodiment of the tissue manipulation device coupled to an embodiment of a second robotic interface.

In other embodiments, the robot, via a second robotic interface 246 (an embodiment of which is illustrated in FIG. 15A), may be directly or indirectly coupled to the tissue manipulation device 10 to displace the wire 52 such that the end effector 48 is displaced from the first undeployed position 49 (illustrated in FIGS. 1 and 6) to the second deployed position 51 (illustrated in FIG. 8). The second robotic interface 246 may be any mechanism, assembly, or device that may interact or interface with the tissue manipulation device 10 to cause (a) the adjustment member 22 (or any portion of the rotational assembly coupled to the adjustment member 22) to rotate and/or (b) the wire 52 to longitudinally displace. For example, in the embodiment of FIG. 15A, the second robotic interface 246 may be a gear 248 that interfaces with the adjustment member 22 (or an equivalent gear that acts as the adjustment member 22) to rotate the adjustment member 22. Instead of a single gear 248, the second robotic interface 246 may include any number or combination of gears to turn the adjustment member 22 to a desired position. In other embodiments, such as that of FIG. 15A, the second robotic interface 246 may be a drive pulley 250 with a belt 252 that is coupled the adjustment member 22 to rotate the adjustment member 22. In some embodiments, the robot will include both the first robotic interface 236 and the second robotic interface 246, or may include either the first robotic interface 236 or the second robotic interface 246.

It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations, therefore, is not intended to limit the claims to any order, except as may be specified in the claims. Accordingly, the invention is limited only by the following claims and equivalents thereto.

What is claimed is:

1. A tissue manipulation device comprising:
a handle portion extending along a longitudinal axis from a proximal end to a distal end;
an adjustment member displaceably coupled to the proximal end of the handle portion;
a securing member coupled to the handle portion, the securing member extending along a member axis from a proximal end to a distal end, the securing member including an engagement portion disposed at or adjacent to the distal end of the securing member, wherein the proximal end of the securing member is coupled to a portion of the adjustment member such that the securing member is displaceable along the member axis between a first securing member position and a second securing member position, wherein the securing member is pivotably coupled to the handle portion and is pivotably displaceable between an engaged position and a disengaged position, and wherein in the engaged position, the member axis is parallel to or coaxially aligned with the longitudinal axis, and in the disengaged position, the member axis is not parallel to or coaxially aligned with the longitudinal axis;
a shaft portion extending from a proximal end to a distal end along a shaft axis, wherein the proximal end of the shaft portion is coupled to the distal end of the handle portion;
an end effector removably coupled to the distal end of the shaft portion, the end effector being operable between a first undeployed position and a second deployed position; and
a flexible wire extending from a proximal end to a distal end, wherein the distal end of the wire is coupled to the end effector, wherein the proximal end of the wire is removably coupled to the engagement portion of the securing member when the securing member is in the engaged position and the proximal end of the wire is disengaged from the engagement portion of the securing member when the securing member is in the disengaged position,
wherein when the securing member is in the engaged position, the wire couples the securing member and the end effector such that (a) when the securing member is displaced from the first securing member position to the second securing member position, the end effector is displaced from the first undeployed position to the second deployed position and (b) when the securing member is displaced from the second securing member position to the first securing member position, the end effector is displaced from the second deployed position to the first undeployed position.

2. The tissue manipulation device of claim 1, wherein when the securing member is in the disengaged position, the end effector is configured to be decoupled from the distal end of the shaft portion and the wire is configured to be removed from the shaft portion through an aperture defined at the distal end of the shaft portion.

3. The tissue manipulation device of claim 1, wherein in the disengaged position, the member axis forms an angle between 1 degree and 180 degrees with the longitudinal axis.

4. The tissue manipulation device of claim 1, wherein the proximal end of the securing member being coupled to a portion of the adjustment member that is at or adjacent to the distal end of the adjustment member.

5. The tissue manipulation device of claim 4, wherein the proximal end of the securing member is biased into engagement with the distal portion of the adjustment member by a resilient member.

6. The tissue manipulation device of claim 5, wherein the resilient member is a spring integrally formed with the securing member.

7. The tissue manipulation device of claim 6, wherein a first end portion of the resilient member is in contact with a post that is fixedly coupled to a portion of the handle portion.

8. The tissue manipulation device of claim 1, wherein at least a portion of the shaft axis is non-linear.

9. The tissue manipulation device of claim 8, wherein the shaft portion includes a linear portion and a curved portion, wherein the linear portion extends from the proximal end of the shaft portion to an intermediate point of the shaft portion, and the curved portion extends from the intermediate point of the shaft portion to the distal end of the shaft portion.

10. The tissue manipulation device of claim 1, wherein the securing member is at least partially disposed in a securing member carrier extending along or parallel to the longitudinal axis from a proximal end to a distal end, wherein the portion of the adjustment member that is at or adjacent to the distal end of the adjustment member is coupled to the proximal end of the securing member carrier, and wherein the securing member is configured to pivot between the engaged position and the disengaged position about a hinge coupled to the securing member carrier.

11. The tissue manipulation device of claim 10, wherein the proximal end of the securing member carrier is biased into engagement with the distal portion of the adjustment member by a resilient member that is a spring integrally formed with the securing member, and wherein a first end portion of the resilient member is in contact with a post that is fixedly coupled to a portion of the handle portion.

12. The tissue manipulation device of claim 11, wherein the hinge is a post that is fixedly coupled to a portion of the securing member carrier, and the post extends through an aperture formed at or adjacent to the proximal end of the securing member.

13. The tissue manipulation device of claim 1, further comprising an adjustment wheel rotatably coupled to a portion of the handle portion, the adjustment wheel being rotatably coupled to a portion of the end effector such that a rotation of the adjustment wheel results in a corresponding rotation of the end effector about an end effector axis relative to the distal end of the shaft portion.

14. The tissue manipulation device of claim 13, wherein the adjustment wheel is coupled to a wheel hub that extends from a proximal end to a distal end and is disposed at least partially within a portion of a wheel housing portion of the handle portion.

15. The tissue manipulation device of claim 14, further comprising a torque member having a proximal end and a distal end, wherein the proximal end of the torque member is engaged with the distal end of the wheel hub, such that a rotation of the wheel hub results in a corresponding rotation of the torque member, and wherein the distal end of the torque member is disposed at or adjacent to a proximal end of a curved portion of the shaft portion.

16. The tissue manipulation device of claim 15, further comprising two or more torque links disposed within the shaft in at least a portion of the curved portion of the shaft portion, wherein the first of the two or more torque links has a proximal end that engages the distal end of the torque member, and a distal end of a most distal of the two or more torque links engages the portion of the end effector such that a rotation of the torque member results in a corresponding rotation of the end effector about the end effector axis relative to the distal end of the shaft portion.

17. The tissue manipulation device of claim 16, wherein the torque member comprises a base that extends along a base axis and a plurality of projections that each extend from the base, wherein the torque member is configured to allow for bending of the torque member about an axis that is normal to the base axis such that the torque member may bend only in a first bending plane.

18. The tissue manipulation device of claim 17, wherein each of the plurality of projections includes an upper projection edge, a lower projection edge, and a lateral edge that cooperate to generally form shape of a wedge.

19. The tissue manipulation device of claim 17, wherein each of the plurality of projections includes a wire bore that extends from a proximal end of each of the plurality of projections to a distal end of each of the plurality of projections, and each of the wire bores in each of the plurality of projections is generally aligned with the other plurality of projections such that a corresponding portion of the wire may be disposed through each of the wire bores.

* * * * *